United States Patent
Honmou et al.

(10) Patent No.: US 10,563,173 B2
(45) Date of Patent: *Feb. 18, 2020

(54) AUTOSERUM-CONTAINING BONE MARROW CELL CULTURE SYSTEM, AUTOSERUM-CONTAINING BONE MARROW CELL CULTURE METHOD, AND METHOD FOR PRODUCING MEDICINAL COMPOSITION COMPRISING AUTOSERUM-CONTAINING CULTURED BONE MARROW CELLS AS ACTIVE INGREDIENT

(71) Applicants: SAPPORO MEDICAL UNIVERSITY, Sapporo-shi (JP); NIPRO CORPORATION, Osaka-shi (JP)

(72) Inventors: Osamu Honmou, Sapporo (JP); Yoshihiro Yoshikawa, Osaka (JP); Naomi Morikawa, Osaka (JP)

(73) Assignee: Nipro Corporation, Osaka (JP)

( * ) Notice: Subject to any disclaimer, the term of this patent is extended or adjusted under 35 U.S.C. 154(b) by 68 days.

This patent is subject to a terminal disclaimer.

(21) Appl. No.: 15/594,991

(22) Filed: May 15, 2017

(65) Prior Publication Data
US 2017/0313984 A1    Nov. 2, 2017

Related U.S. Application Data

(63) Continuation of application No. 13/813,766, filed as application No. PCT/JP2011/067758 on Aug. 3, 2011, now Pat. No. 9,683,214.

(30) Foreign Application Priority Data

| Aug. 3, 2010 | (JP) | 2010-174902 |
| Aug. 3, 2010 | (JP) | 2010-174903 |
| Sep. 29, 2010 | (JP) | 2010-218275 |

(51) Int. Cl.
- *C12N 5/0775* (2010.01)
- *A61M 1/02* (2006.01)
- *A61K 35/28* (2015.01)

(52) U.S. Cl.
CPC ........... *C12N 5/0663* (2013.01); *A61K 35/28* (2013.01); *A61M 1/0272* (2013.01); *A61M 2202/10* (2013.01)

(58) Field of Classification Search
CPC .............................................. A61M 1/0272
See application file for complete search history.

(56) References Cited

U.S. PATENT DOCUMENTS

| 3,748,101 A | 7/1973 | Jones et al. |
| 2005/0239196 A1 | 10/2005 | Yanai et al. |
| 2008/0171951 A1 | 7/2008 | Fell |
| 2010/0254953 A1 | 10/2010 | Honmou et al. |

FOREIGN PATENT DOCUMENTS

| CA | 2 535 034 A1 | 1/2005 |
| JP | 2004-008110 A | 1/2004 |
| JP | 2004-073084 A | 3/2004 |
| JP | 2004-073187 A | 3/2004 |
| JP | 2006-055106 A | 3/2006 |
| JP | 2008-538514 A | 10/2008 |
| JP | 2009-065854 A | 4/2009 |
| JP | 2009-065884 A | 4/2009 |
| JP | 2009-077879 A | 4/2009 |
| JP | 2009-100719 A | 5/2009 |
| WO | WO 2005/007176 A1 | 1/2005 |
| WO | WO 2006/022091 A1 | 3/2006 |
| WO | WO 2006/123645 A1 | 11/2006 |
| WO | WO 2009/034708 A1 | 3/2009 |

OTHER PUBLICATIONS

Kobayashi et al. J Bone Joint Surg., 2005, 87-B:1426-1433.*
[JP,2009-100719, A]—machine translation.
Causse et al., Journal of Chromatography A, 895(1-2):173-78 (2000).
Colter et al., Proceedings of the National Academy of Sciences, 97(7):3213-18 (2000).
Corrected Machine Translation for JP 2009-100719 dated May 14, 2009.
Koshihara et al., J of endocrinology, 176:339-48 (2003).
Lee et al., International J of Laboratory Hematology, 30:349-65 (2008).
Lin et al., Transplantation Proceedings, 37:4504-505 (2005).
Neuner et al., Veterinary Immunology and Immunopathology, 61:1-16 (1998).
Novotny et al., Clin. Lab. Haem., 27:33-40 (2005).
PCT/JP2011/067758 International Search Report issued by Japanese Patent Office dated Oct. 19, 2011.

* cited by examiner

*Primary Examiner* — Bin Shen
(74) *Attorney, Agent, or Firm* — RatnerPrestia

(57) ABSTRACT

To provide an autoserum-containing bone marrow cell culture system, whereby bone marrow cells, which are collected from a subject without using an anticoagulant, are subjected to an anticoagulation treatment using a medium in a liquid-tight state, cultured and then further cultured using the serum of said subject which is prepared in a liquid-tight state; an autoserum-containing bone marrow cell culture method; and a method for producing a medicinal composition which comprises, as the active ingredient, autoserum-containing cultured bone marrow cells. [Solution] An autoserum-containing bone marrow cell culture system for culturing bone marrow cells, which are collected from a subject without using an anticoagulant, using the serum of said subject, said system comprising a bone marrow cell suspension-storing device, a collected blood-storing device, an autoserum-acquiring device, and a bone marrow cell-culturing device.

10 Claims, 12 Drawing Sheets

AUTOSERUM-CONTAINING BONE MARROW CELL CULTURE SYSTEM, AUTOSERUM-CONTAINING BONE MARROW CELL CULTURE METHOD, AND METHOD FOR PRODUCING MEDICINAL COMPOSITION COMPRISING AUTOSERUM-CONTAINING CULTURED BONE MARROW CELLS AS ACTIVE INGREDIENT

CROSS-REFERENCE TO RELATED APPLICATIONS

This application is a continuation of U.S. application Ser. No. 13/813,766, filed Feb. 1, 2013, now U.S. Pat. No. 9,683,214, which is a U.S. National Phase Application of PCT International Application No. PCT/JP2011/067758, filed Aug. 3, 2011 and amended on Apr. 5, 2012, which claims priority to Japanese Application Nos. 2010-174903, filed Aug. 3, 2010, 2010-174902, filed Aug. 3, 2010, and 2010-218275, filed Sep. 29, 2010, the contents of which are incorporated herein by reference in their entireties for all purposes.

TECHNICAL FIELD

The present invention relates to an autoserum-containing bone marrow cell culture system, an autoserum-containing bone marrow cell culture method, and a method for producing a medicinal composition comprising autoserum-containing cultured bone marrow cells as an active ingredient. More specifically, the present invention relates to an autoserum-containing bone marrow cell culture system and an autoserum-containing bone marrow cell culture method for culturing bone marrow cells collected from a subject without use of an anticoagulant with the serum of the subject, and a method for producing a medicinal composition comprising, as an active ingredient, autoserum-containing cultured bone marrow cells obtained by collecting bone marrow cells from a subject without use of an anticoagulant and culturing the cells with the serum of the subject.

BACKGROUND OF THE INVENTION

A method which involves intravenously administering bone marrow cells of mononuclear cell fractions obtained from the bone marrow of a patient to the patient has been developed as part of regenerative medicine to treat cranial nerve disease such as cerebral infarction, spinal cord injury and demyelinating disease (Patent Literature 1). This treatment method is easy to practice from the viewpoint of administering the cells to the vein without directly administering the cells to an affected area and, advantageously, can be performed conveniently in general medical settings.

For such a treatment method, it is important to secure bone marrow cells in an amount sufficient for intravenous administration to a patient. Examples of such techniques can include a system which involves collecting bone marrow cells from a patient, then directly acquiring the bone marrow cells in an aseptic manner or liquid-tightly acquiring the bone marrow cells, and administering the cells to the patient (Patent Literature 2), and a method which involves culturing bone marrow cells contained in a collected bone marrow fluid in a medium containing heparin or human serum (Patent Literature 3). According to the previous reports, bone marrow cells are preferably cultured using the serum of a patient who is a donor of the bone marrow cells, from the viewpoint of compatibility and safety (Patent Literatures 4, 5, and 6).

CITATION LIST

Patent Literature

Patent Literature 1: International Publication No. WO2005/007176
Patent Literature 2: National Publication of International Patent Application No. 2008-538514
Patent Literature 3: Japanese Patent Laid-Open No. 2006-055106
Patent Literature 4: Japanese Patent Laid-Open No. 2009-065854
Patent Literature 5: Japanese Patent Laid-Open No. 2009-065884
Patent Literature 6: International Publication No. WO2009/034708

SUMMARY OF THE INVENTION

Technical Problem

Since a bone marrow fluid collected from a patient coagulates rapidly, an anticoagulant such as heparin is used to inhibit this coagulation reaction. Usually, it is difficult for health-care professionals to immediately culture bone marrow cells at the site where the bone marrow fluid is collected from the patient. In addition, the bone marrow cells should be cultured at a cell processing center (CPC), which is the location of cell culture distant from the site of bone marrow collection, because of the need to ensure the effects and safety of the cultured bone marrow cells. For these reasons, the anticoagulant must be used inevitably. The anticoagulant such as heparin, however, has been found to have significant inhibitory effects on cell growth.

In recent years, regenerative medicine settings associated with the treatment of cranial nerve disease such as cerebral infarction, spinal cord injury and demyelinating disease have further required culturing bone marrow cells cleanly, safely, reliably, and highly efficiently. None of the conventional systems or methods satisfies such needs.

The present invention has been made to solve these problems, and an object of the present invention is to provide an autoserum-containing bone marrow cell culture system and an autoserum-containing bone marrow cell culture method for anticoagulating and culturing bone marrow cells collected from a subject without use of an anticoagulant in a liquid-tight state using a medium and further culturing the resulting bone marrow cells with the serum of the subject prepared in a liquid-tight state, and a method for producing a medicinal composition comprising autoserum-containing cultured bone marrow cells as an active ingredient.

Solution to Problem

As a result of conducting diligent studies, the present inventors have found that the coagulation reaction can be suppressed for a sufficient period by mixing a bone marrow fluid containing bone marrow cells collected from a subject with a minimal amount of a medium. The present inventors have also found that bone marrow cells can be cultured cleanly, safely, reliably, and highly efficiently by mixing the bone marrow fluid with the medium in a liquid-tight state at the site of bone marrow collection to prepare an anticoagulated bone marrow cell suspension, and transporting the suspension in this state to CPC where the bone marrow cells are then cultured, followed by culture using the autoserum of the subject prepared in a liquid-tight state, or by mixing a bone marrow fluid containing bone marrow cells collected from the subject with a medium in a liquid-tight state at the site of bone marrow collection to prepare anticoagulated bone marrow cell suspension, directly culturing the bone marrow cells, and transporting the resulting cells to CPC, followed by further culture using the autoserum of the subject prepared in a liquid-tight state. On the basis of these findings, the present invention according to the following aspects has been completed:

(1) An autoserum-containing bone marrow cell culture system for culturing bone marrow cells collected from a subject without use of an anticoagulant with the serum of the subject, wherein: a bone marrow fluid containing bone marrow cells collected from the subject is transferred at the site of collection from a bone marrow fluid storing syringe where the bone marrow fluid is stored to a bone marrow cell suspension transporting vessel which is a liquid-tightly sealable rigid vessel, and then anticoagulated by mixing with a medium; the anticoagulated bone marrow cell suspension thus obtained by the mixing of the bone marrow fluid with the medium is transported in a suspended state while stored in the bone marrow cell suspension transporting vessel, and then transferred to a bone marrow cell culture vessel which cultures the bone marrow cells at the location of cell culture, to start culture; after a lapse of a predetermined culture period, the culture supernatant is removed; and a medium and the serum of the subject are added into the bone marrow cell culture vessel to perform further culture.

(2) The autoserum-containing bone marrow cell culture system according to (1), comprising at least one of the following devices (a), (b), (c), and (d): (a) a bone marrow cell suspension storing device having the bone marrow fluid storing syringe, a medium storing syringe which stores a medium, the bone marrow cell suspension transporting vessel which stores the bone marrow cell suspension, and a connecting unit for bone marrow cell suspension which is capable of distributing the bone marrow fluid and the medium and capable of liquid-tightly connecting the bone marrow fluid storing syringe, the medium storing syringe, and the bone marrow cell suspension transporting vessel; (b) a blood collecting and storing device having a vascular puncture needle which is inserted to the blood vessel of the subject, a liquid-tightly sealable blood storing vessel which stores the blood of the subject and is capable of being centrifuged, and a connecting unit for blood collection which is capable of distributing blood and capable of liquid-tightly connecting the vascular puncture needle and the blood storing vessel; (c) an autoserum acquiring device having a centrifuging unit which centrifuges the blood storing vessel where the blood of the subject is stored to obtain the serum of the subject; and (d) a bone marrow cell culturing device having the bone marrow cell culture vessel.

(3) The autoserum-containing bone marrow cell culture system according to (1), comprising the following devices (a), (b), (c), and (d): (a) a bone marrow cell suspension storing device having the bone marrow fluid storing syringe, a medium storing syringe which stores a medium, the bone marrow cell suspension transporting vessel which stores the bone marrow cell suspension, and a connecting unit for bone marrow cell suspension which is capable of distributing the bone marrow fluid and the medium and capable of liquid-tightly connecting the bone marrow fluid storing syringe, the medium storing syringe, and the bone marrow cell suspension transporting vessel; (b) a blood collecting and storing device having a vascular puncture needle which is inserted to the blood vessel of the subject, a liquid-tightly sealable blood storing vessel which stores the blood of the subject and is capable of being centrifuged, and a connecting unit for blood collection which is capable of distributing blood and capable of liquid-tightly connecting the vascular puncture needle and the blood storing vessel; (c) an autoserum acquiring device having a centrifuging unit which centrifuges the blood storing vessel where the blood of the subject is stored to obtain the serum of the subject; and (d) a bone marrow cell culturing device having the bone marrow cell culture vessel.

(4) The autoserum-containing bone marrow cell culture system according to (2) or (3), wherein the bone marrow cell suspension transporting vessel has the following components (e) and (f) and the connecting unit for bone marrow cell suspension has the following component (g): (e) a transporting vessel tube which communicates the connecting unit for bone marrow cell suspension with the interior space of the bone marrow cell suspension transporting vessel; (f) a transporting vessel vent which communicates the interior space of the bone marrow cell suspension transporting vessel with exterior space and is provided at its tip with a transporting vessel vent filter that prevents bacteria from entering the vent; and (g) a three-way stopcock for bone marrow cell suspension having three connecting ports, i.e., a first port for suspension, a second port for suspension, and a third port for suspension, and a cock for suspension which selectively communicates two of these connecting ports.

(5) The autoserum-containing bone marrow cell culture system according to any of (2) to (4), wherein the blood storing vessel has the following components (h) and (i): (h) a storing vessel tube which communicates the connecting unit for blood collection with the interior space of the blood storing vessel; and (i) a storing vessel vent which communicates the interior space of the blood storing vessel with exterior space and is provided at its tip with a storing vessel vent filter that prevents bacteria from entering the vent.

(6) The autoserum-containing bone marrow cell culture system according to any of (2) to (4), wherein the blood collecting and storing device is a blood collecting and storing device having: an indwelling needle which is a blood collection needle capable of maintaining a state inserted to the blood vessel of the subject; an indwelling needle connection tube connected with the indwelling needle; a liquid-tightly sealable blood storing vessel which stores the blood of the subject and is capable of being centrifuged and has the following components (j) and (k); a syringe for blood collection which is capable of collecting and storing blood from the subject in a liquid-tight state and capable of pushing the blood out; and a three-way connecting unit for blood collection which is capable of distributing blood and capable of liquid-tightly connecting the indwelling needle connection tube connected with the indwelling needle, the syringe for blood collection, and the blood storing vessel, and has the following component (l): (j) a storing vessel tube which communicates the three-way connecting unit for blood collection with the interior space of the blood storing vessel; (k) a storing vessel vent which communicates the interior space of the blood storing vessel with exterior space and is provided at its tip with a storing vessel vent filter that prevents bacteria from entering the vent; and (l) a three-way stopcock for blood collection having three connecting ports, i.e., a first port for blood collection, a second port for blood collection, and a third port for blood collection, and a cock for blood collection which selectively communicates two of these connecting ports.

(7) The autoserum-containing bone marrow cell culture system according to any of (1) to (6), wherein the culture is started by the addition of a medium and/or the serum of the subject when the bone marrow cell suspension is transferred to the bone marrow cell culture vessel.

(8) An autoserum-containing bone marrow cell culture system for culturing bone marrow cells collected from a subject without use of an anticoagulant with the serum of the subject, wherein: a bone marrow fluid containing bone marrow cells collected from the subject is transferred at the site of collection from a bone marrow fluid storing syringe where the bone marrow fluid is stored to a bone marrow cell culturing and transporting vessel which is a liquid-tightly sealable rigid vessel that stores an anticoagulated bone marrow cell suspension obtained by mixing the bone marrow fluid with a medium and starts culture of the bone marrow cells, and then mixed with the medium to perform anticoagulation while starting culture of the bone marrow cells; the resulting bone marrow cell suspension is transported in a cultured state while stored in the bone marrow cell culturing and transporting vessel; after a lapse of a predetermined culture period, the culture supernatant is removed; and at the location of cell culture, a medium and the serum of the subject are added into the bone marrow cell culturing and transporting vessel to perform further culture.

(9) The autoserum-containing bone marrow cell culture system according to (8), comprising at least one of the following devices (i), (ii), and (iii): (i) a bone marrow cell culturing device having the bone marrow fluid storing syringe, a medium storing syringe which stores a medium, the bone marrow cell culturing and transporting vessel, and a connecting unit for bone marrow cell suspension which is capable of distributing the bone marrow fluid and the medium and capable of liquid-tightly connecting the bone marrow fluid storing syringe, the medium storing syringe, and the bone marrow cell culturing and transporting vessel; (ii) a blood collecting and storing device having a vascular puncture needle which is inserted to the blood vessel of the subject, a liquid-tightly sealable blood storing vessel which stores the blood of the subject and is capable of being centrifuged, and a connecting unit for blood collection which is capable of distributing blood and capable of liquid-tightly connecting the vascular puncture needle and the blood storing vessel; and (iii) an autoserum acquiring device having a centrifuging unit which centrifuges the blood storing vessel where the blood of the subject is stored to obtain the serum of the subject.

(10) The autoserum-containing bone marrow cell culture system according to (8), comprising the following devices (i), (ii), and (iii): (i) a bone marrow cell culturing device having the bone marrow fluid storing syringe, a medium storing syringe which stores a medium, the bone marrow cell culturing and transporting vessel, and a connecting unit for bone marrow cell suspension which is capable of distributing the bone marrow fluid and the medium and capable of liquid-tightly connecting the bone marrow fluid storing syringe, the medium storing syringe, and the bone marrow cell culturing and transporting vessel; (ii) a blood collecting and storing device having a vascular puncture needle which is inserted to the blood vessel of the subject, a liquid-tightly sealable blood storing vessel which stores the blood of the subject and is capable of being centrifuged, and a connecting unit for blood collection which is capable of distributing blood and capable of liquid-tightly connecting the vascular puncture needle and the blood storing vessel; and (iii) an autoserum acquiring device having a centrifuging unit which centrifuges the blood storing vessel where the blood of the subject is stored to obtain the serum of the subject.

(11) The autoserum-containing bone marrow cell culture system according to (9) or (10), wherein the bone marrow cell culturing and transporting vessel has the following components (iv) and (v) and the connecting unit for bone marrow cell suspension has the following component (vi): (iv) a culturing and transporting vessel tube which communicates the connecting unit for bone marrow cell suspension with the interior space of the bone marrow cell culturing and transporting vessel; (v) a culturing and transporting vessel vent which communicates the interior space of the bone marrow cell culturing and transporting vessel with exterior space and is provided at its tip with a culturing and transporting vessel vent filter that prevents bacteria from entering the vent; and (vi) a three-way stopcock for bone marrow cell suspension having three connecting ports, i.e., a first port for suspension, a second port for suspension, and a third port for suspension, and a cock for suspension which selectively communicates two of these connecting ports.

(12) The autoserum-containing bone marrow cell culture system according to any of (9) to (11), wherein the blood storing vessel has the following components (vii) and (viii): (vii) a storing vessel tube which communicates the connecting unit for blood collection with the interior space of the blood storing vessel; and (viii) a storing vessel vent which communicates the interior space of the blood storing vessel with exterior space and is provided at its tip with a storing vessel vent filter that prevents bacteria from entering the vent.

(13) The autoserum-containing bone marrow cell culture system according to any of (9) to (11), wherein the blood collecting and storing device is a blood collecting and storing device having: an indwelling needle which is a blood collection needle capable of maintaining a state inserted to the blood vessel of the subject; an indwelling needle connection tube connected with the indwelling needle; a liquid-tightly sealable blood storing vessel which stores the blood of the subject and is capable of being centrifuged and has the following components and (x); a syringe for blood collection which is capable of collecting and storing blood from the subject in a liquid-tight state and capable of pushing the blood out; and a three-way connecting unit for blood collection which is capable of distributing blood and capable of liquid-tightly connecting the indwelling needle connection tube connected with the indwelling needle, the syringe for blood collection, and the blood storing vessel and has the following component (xi): (ix) a storing vessel tube which communicates the three-way connecting unit for blood collection with the interior space of the blood storing vessel; (x) a storing vessel vent which communicates the interior space of the blood storing vessel with exterior space and is provided at its tip with a storing vessel vent filter that prevents bacteria from entering the vent; and (xi) a three-way stopcock for blood collection having three connecting ports, i.e., a first port for blood collection, a second port for blood collection, and a third port for blood collection, and a cock for blood collection which selectively communicates two of these connecting ports.

(14) A method for culturing bone marrow cells collected from a subject without use of an anticoagulant with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a liquid-tight state at the site of collection of the bone marrow fluid to prepare an anticoagulant-free bone marrow cell suspension; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a bone marrow cell culture step in which the bone marrow cells contained in the prepared bone marrow cell suspension are cultured in a bone marrow cell culture vessel; a culture supernatant removal step in which the culture supernatant containing floating cells is removed from the bone marrow cell culture vessel with the thus-cultured bone marrow cells attached thereto; and an autoserum medium addition step in which the obtained serum of the subject and a medium are added to the bone marrow cell culture vessel with the bone marrow cells attached thereto.

(15) A method for culturing bone marrow cells collected from a subject without use of an anticoagulant with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a liquid-tight state at the site of collection of the bone marrow fluid to prepare an anticoagulant-free bone marrow cell suspension; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a bone marrow cell suspension mixture preparation step in which the prepared bone marrow cell suspension is mixed with a medium and/or the obtained serum of the subject to prepare a bone marrow cell suspension mixture; a bone marrow cell culture step in which the bone marrow cells contained in the prepared bone marrow cell suspension mixture are cultured in a bone marrow cell culture vessel; a culture supernatant removal step in which the culture supernatant containing floating cells is removed from the bone marrow cell culture vessel with the thus-cultured bone marrow cells attached thereto; and an autoserum medium addition step in which the obtained serum of the subject and a medium are added to the bone marrow cell culture vessel with the bone marrow cells attached thereto.

(16) The method according to (15), wherein the total amount of the media mixed with the bone marrow fluid in the bone marrow cell suspension mixture or the total sum of the amount of the medium or media mixed with the bone marrow fluid and the amount of the obtained serum of the subject mixed with the bone marrow fluid in the bone marrow cell suspension mixture is 4 times to 80 times the amount of the bone marrow fluid.

(17) The method according to any of (14) to (16), wherein the amount appropriate for the amount of the bone marrow fluid is 1.5 times to 6 times the amount of the bone marrow fluid.

(18) The method according to any of (14) to (17), wherein the bone marrow cells contained in the bone marrow cell suspension or the bone marrow cell suspension mixture are cultured for 4 days to 7 days in the bone marrow cell culture vessel.

(19) A method for directly culturing bone marrow cells collected from a subject without use of an anticoagulant and further culturing the resulting cells with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a bone marrow cell culturing and transporting vessel with a liquid-tight state at the site of collection of the bone marrow fluid to prepare an anticoagulant-free bone marrow cell suspension; a bone marrow cell culture and transport step in which the bone marrow cells contained in the prepared bone marrow cell suspension are transported to the location of cell culture while cultured in the bone marrow cell culturing and transporting vessel; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a culture supernatant removal step in which the culture supernatant containing floating cells is removed from the bone marrow cell culturing and transporting vessel with the thus-cultured bone marrow cells attached thereto; and an autoserum medium addition step in which the serum of the subject and a medium are added to the bone marrow cell culturing and transporting vessel with the bone marrow cells attached thereto.

(20) The method according to (19), wherein the bone marrow cell culturing and transporting vessel is a cell culture flask.

(21) The method according to (19) or (20), wherein the amount appropriate for the amount of the bone marrow fluid is 2 times to 4 times the amount of the bone marrow fluid.

(22) The method according to any of (19) to (21), wherein the bone marrow cells contained in the prepared bone marrow cell suspension are cultured for 4 days to 7 days in the bone marrow cell culturing and transporting vessel.

(23) The method according to any of (14) to (22), wherein the blood storing vessel is a rigid vessel.

(24) A method for producing a medicinal composition comprising, as an active ingredient, bone marrow cells that have been collected from a subject without use of an anticoagulant and cultured with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a liquid-tight state at the site of collection of the bone marrow fluid to prepare an anticoagulant-free bone marrow cell suspension; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a bone marrow cell culture step in which the bone marrow cells contained in the prepared bone marrow cell suspension are cultured in a bone marrow cell culture vessel; a culture supernatant removal step in which the culture supernatant containing floating cells is removed from the bone marrow cell culture vessel with the thus-cultured bone marrow cells attached thereto; and an autoserum medium addition and culture step in which the obtained serum of the subject and a medium are added to the bone marrow cell culture vessel with the bone marrow cells attached thereto to culture the cells.

(25) A method for producing a medicinal composition comprising, as an active ingredient, bone marrow cells that have been collected from a subject without use of an anticoagulant and cultured with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a liquid-tight state at the site of collection of the bone marrow fluid to prepare an anticoagulant-free bone marrow cell suspension; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a bone marrow cell suspension mixture preparation step in which the prepared bone marrow cell suspension is mixed with a medium and/or the obtained serum of the subject to prepare a bone marrow cell suspension mixture; a bone marrow cell culture step in which the bone marrow cells contained in the prepared bone marrow cell suspension mixture are cultured in a bone marrow cell culture vessel; a culture supernatant removal step in which the culture supernatant containing floating cells is removed from the bone marrow cell culture vessel with the thus-cultured bone marrow cells attached thereto; and an autoserum medium addition and culture step in which the obtained serum of the subject and a medium are added to the bone marrow cell culture vessel with the bone marrow cells attached thereto to culture the cells.

(26) A method for producing a medicinal composition comprising, as an active ingredient, bone marrow cells that have been collected from a subject without use of an anticoagulant, then directly cultured, and further cultured with the serum of the subject, comprising: a bone marrow cell suspension preparation step in which a bone marrow fluid containing bone marrow cells collected from the subject is anticoagulated by mixing with a medium in an amount appropriate for the amount of the bone marrow fluid in a bone marrow cell culturing and transporting vessel with a liquid-tight state at the site of collection of the bone marrow fluid to prepare an anticoagulant-free bone marrow cell suspension; a bone marrow cell culture and transport step in which the bone marrow cells contained in the prepared bone marrow cell suspension are transported to the location of cell culture while cultured in the bone marrow cell culturing and transporting vessel; a blood collection and storage step in which blood is collected from the subject without addition of an anticoagulant and stored in a liquid-tight state in a blood storing vessel capable of being centrifuged; an autoserum acquisition step in which the blood storing vessel where the blood of the subject is stored is centrifuged to obtain the serum of the subject; a culture supernatant removal step in which the culture supernatant containing floating cells is removed from the bone marrow cell culturing and transporting vessel with the thus-cultured bone marrow cells attached thereto; and an autoserum medium addition and culture step in which the serum of the subject and a medium are added to the bone marrow cell culturing and transporting vessel with the bone marrow cells attached thereto to culture the cells.

Advantageous Effects of Invention

According to the present invention, bone marrow cells can be collected and cultured cleanly, safely, reliably, and highly efficiently in regenerative medicine settings associated with the treatment of cranial nerve disease such as cerebral infarction, spinal cord injury and demyelinating disease. In addition, a medicinal composition comprising, as an active ingredient, an autoserum-containing cultured bone marrow cells that has been collected and cultured cleanly, safely, reliably, and highly efficiently can be obtained.

DETAILED DESCRIPTION OF THE INVENTION

Figure 1:
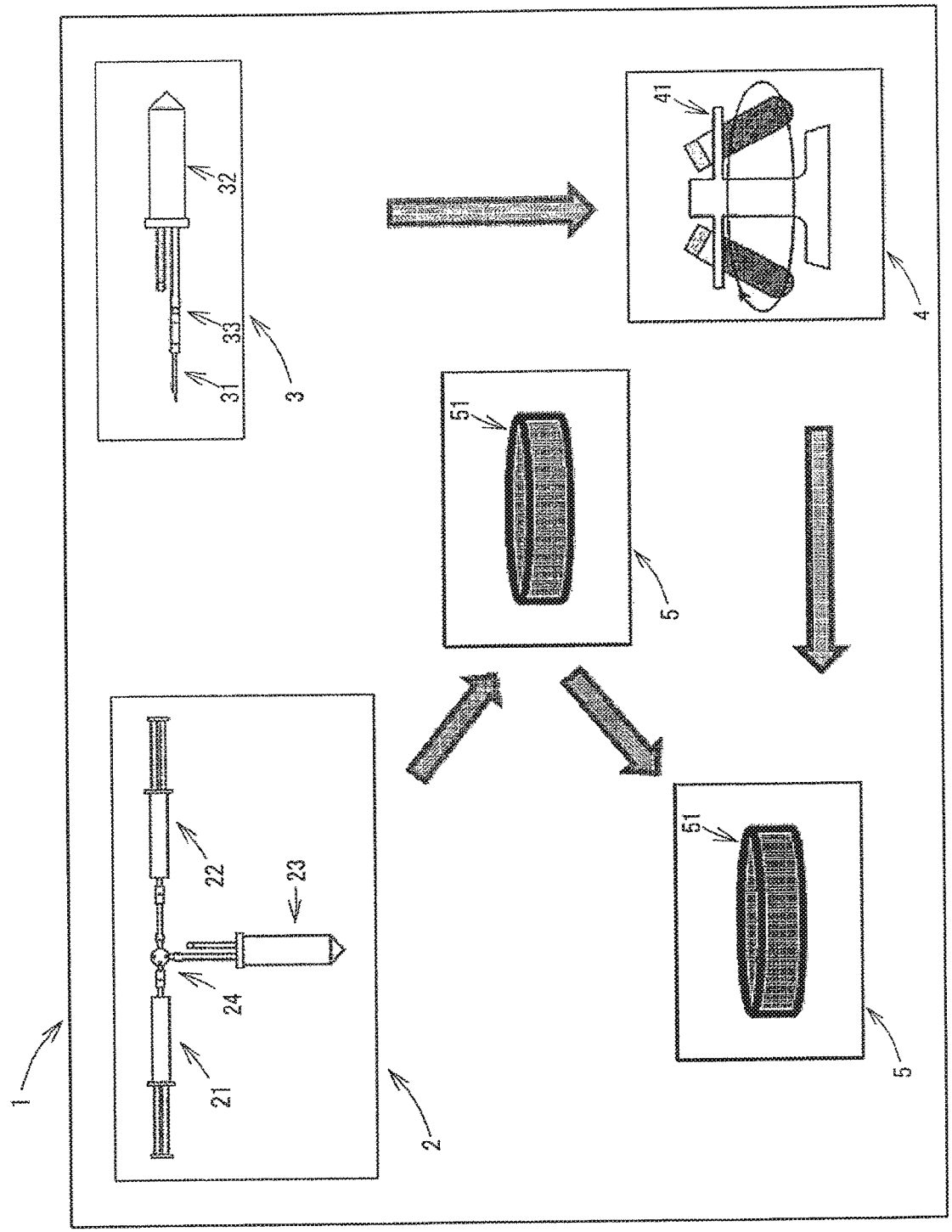
FIG. 1 is a diagram showing the first embodiment of the autoserum-containing bone marrow cell culture system according to the present invention.

Hereinafter, the autoserum-containing bone marrow cell culture system, the autoserum-containing bone marrow cell culture method, and the method for producing a medicinal composition comprising autoserum-containing cultured bone marrow cells as an active ingredient according to the present invention will be described in detail. In the first embodiment, an autoserum-containing bone marrow cell culture system 1 according to the present invention is an autoserum-containing bone marrow culture system for culturing bone marrow cells collected from a subject without use of an anticoagulant with the serum of the subject, wherein: a bone marrow fluid containing bone marrow cells collected from the subject is transferred at the site of collection from a bone marrow fluid storing syringe 21 where the bone marrow fluid is stored to a bone marrow cell suspension transporting vessel 23 which is a liquid-tightly sealable rigid vessel, and then anticoagulated by mixing with a medium; the anticoagulated bone marrow cell suspension thus obtained by the mixing of the bone marrow fluid with the medium is transported in a suspended state while stored in the bone marrow cell suspension transporting vessel 23, and then transferred to a bone marrow cell culture vessel 51 which cultures the bone marrow cells at the location of cell culture, to start culture; after a lapse of a predetermined culture period, the culture supernatant is removed; and a medium and the serum of the subject are added into the bone marrow cell culture vessel 51 to perform further culture.

In the first embodiment, the autoserum-containing bone marrow cell culture system 1 according to the present invention preferably comprises at least one of a bone marrow cell suspension storing device 2, a blood collecting and storing device 3, an autoserum acquiring device 4, and a bone marrow cell culturing device 5 and more preferably comprises all of these devices.

The bone marrow cell suspension storing device 2 is constituted mainly of a bone marrow fluid storing syringe 21, a medium storing syringe 22, a bone marrow cell suspension transporting vessel 23, and a connecting unit 24 for bone marrow cell suspension.

The bone marrow fluid storing syringe 21 is not particularly limited as long as the syringe is capable of collecting, storing a bone marrow fluid containing bone marrow cells from the subject and pushing the bone marrow fluid out in a liquid-tight state. Examples thereof can include those usually used in the medical field.

The medium storing syringe 22 is not particularly limited as long as the syringe is capable of storing a medium and pushing the medium out in a liquid-tight state. Examples thereof can include those usually used in the medical field. In the present first embodiment, a syringe similar to the bone marrow fluid storing syringe 21 can be used.

In the present invention, the medium can be selected appropriately according to the type, desired direction or level of differentiation, required growth rate, etc., of the bone marrow cells. Examples of media suitable for growing mesenchymal stem cells such as bone-marrow stromal cells for use in the repair of the nervous system can include, but not limited to, a Dulbecco's modified eagle's medium (DMEM) shown below as well as a neural progenitor basal medium (NPBM; Clontech Laboratories, Inc.) and an α-MEM medium.

Composition of DMEM: <Concentration (mg/L)>

$CaCl_2$ (anhydride) <160 to 240>, KCL <320 to 480>, $Fe(NO_3)_3 \cdot 9H_2O$ <0.08 to 1.2>, $MgSO_4$ (anhydride) <80 to 120>, NaCl <5120 to 7680>, $NaHCO_3$ <2960 to 4440>, $NaH_2PO_4 \cdot H_2O$ <100 to 150>, D-glucose <3600 to 5400>, phenol red <12 to 18>, sodium pyruvate <88 to 132>, L-arginine.HCl <67 to 101>, L-cysteine.2HCl <50 to 76>, L-histidine.HCl.$H_2O$ <34 to 50>, L-isoleucine <84 to 126>, L-leucine <84 to 126>, L-lysine.HCl <117 to 175>, L-methionine <24 to 36>, L-phenylalanine <53 to 79>, L-serine <34 to 50>, L-threonine <76 to 114>, L-tryptophan <13 to 19>, L-tyrosine (disodium salt) <83 to 125>, L-valine <75 to 113>, choline chloride <3.2 to 4.8>, D-Ca-pantothenic acid <3.2 to 4.8>, folic acid <3.2 to 4.8>, i-inositol <5.8 to 8.6>, niacinamide <3.2 to 4.8>, pyridoxal.HCl <3.2 to 4.8>, riboflavin <0.3 to 0.5>, and thiamine.HCl <3.2 to 4.8>.

In the present invention, the medium may be further supplemented with serum, a nutritional factor, a proliferative factor, a growth factor, a differentiation-inducing factor, an antibiotic, an amino acid, and the like, if necessary. The concentrations of these substances added to the medium can be set appropriately according to the desired direction or level of differentiation, required growth rate, etc., of the bone marrow cells.

Specific examples of the nutritional factor, the proliferative factor, the growth factor, and the differentiation-inducing factor can include: vitamins such as ascorbic acid and nicotinamide; neurotrophic factors such as NGF and BDNF; bone morphogenetic factors such as BMP; epithelial cell growth factors; basic fibroblast growth factors; insulin-like growth factors, and cytokines such as IL-2.

Examples of the antibiotic can include penicillin and streptomycin. These antibiotics may be added alone or in combination to the medium. The concentration of the antibiotic added thereto can be, for example, 0.5 to 2% (v/v), preferably 0.8 to 1.2% (v/v), of each antibiotic with respect to the total amount of the medium when penicillin and streptomycin are added in combination.

Examples of the amino acid can include L-alanine, L-aspartic acid, L-cysteine, L-glutamine, L-isoleucine, L-methionine, L-phenylalanine, L-proline, L-serine, L-threonine, L-tyrosine, L-valine, L-ascorbic acid, and L-glutamic acid. The concentration of the amino acid added to the medium can be, for example, 0.1 to 2% (w/v) of L-glutamine with respect to the total amount of the medium for the rapid growth of mesenchymal stem cells.

Figure 2:
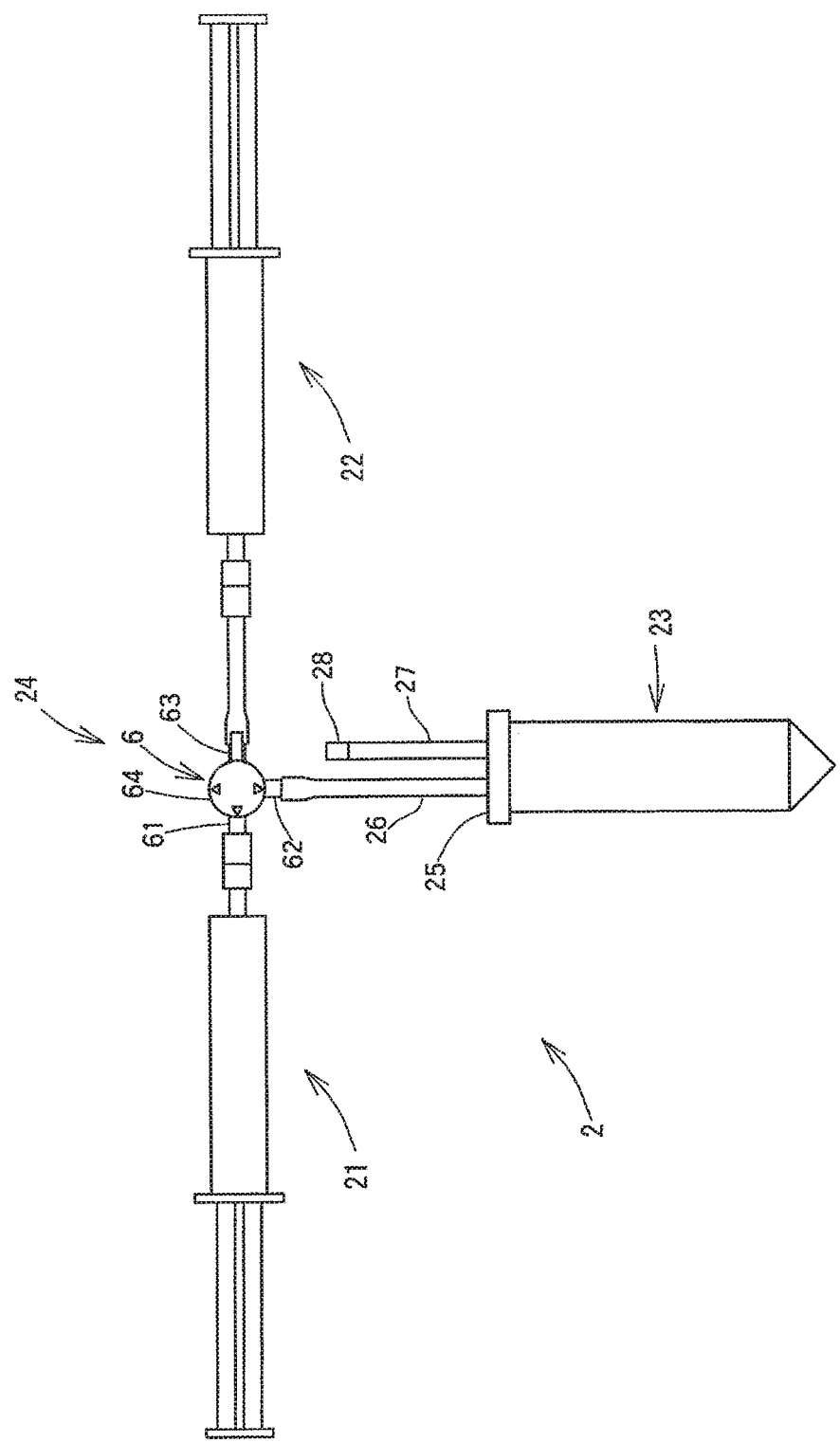
FIG. 2 is a diagram showing a bone marrow cell suspension storing device of the first embodiment according to the present invention.

The bone marrow cell suspension transporting vessel 23 is not particularly limited as long as the vessel is a liquid-tightly sealable rigid vessel capable of storing an anticoagulated bone marrow cell suspension obtained by mixing the bone marrow fluid with the medium. Examples of such constitution can include constitution in which, as shown in FIG. 2, the bone marrow cell suspension transporting vessel 23 has an open upper end to which a transporting vessel lid 25 is fastened in a liquid-tightly sealable manner with screws, the transporting vessel lid 25 comprising a transporting vessel tube 26 and a transporting vessel vent 27. The transporting vessel tube 26 communicates the connecting unit 24 for bone marrow cell suspension with the interior space of the bone marrow cell suspension transporting vessel 23. The transporting vessel vent 27 communicates the interior space of the bone marrow cell suspension transporting vessel 23 with exterior space. The transporting vessel vent 27 is provided at its tip with a transporting vessel vent filter 28 that prevents bacteria from entering the vent.

In the present invention, the terms "medium" and "culture solution" may be used interchangeably. Likewise, the terms "anticoagulation" and "anticoagulation treatment" or the terms "coagulation termination" and "coagulation inhibition" may be used interchangeably.

In the present invention, examples of materials constituting the rigid vessel can include metals and glass as well as somewhat flexible resins such as polypropylene, polyvinyl chloride, and polystyrene. Also, examples of materials constituting the transporting vessel tube 26 can include those sealable in a liquid-tight state by sealing with a commercially available heat sealer, clip, or the like. Also, examples of the transporting vessel vent filter 28 can include a depth-type filter capable of capturing bacteria within the filter, and a screen-type filter capable of capturing bacteria on the filter surface.

The connecting unit 24 for bone marrow cell suspension is not limited as long as the unit is constitutionally or functionally capable of distributing the bone marrow fluid and the medium and capable of liquid-tightly connecting the bone marrow fluid storing syringe 21, the medium storing syringe 22, and the bone marrow cell suspension transporting vessel 23. Examples of such constitution can include constitution having, as shown in FIG. 2, a three-way stopcock 6 for bone marrow cell suspension. The three-way stopcock 6 for bone marrow cell suspension has three connecting ports, i.e., a first port 61 for suspension, a second port 62 for suspension, and a third port 63 for suspension, and a cock 64 for suspension which selectively communicates two of these connecting ports. The cock 64 for suspension can be turned to change its posture at least to a posture by which the first port 61 for suspension and the second port 62 for suspension are communicated with each other and a posture by which the second port 62 for suspension and the third port 63 for suspension are communicated with each other. For example, a general T-shaped medical three-way stopcock as well as the stopcock described in Japanese Patent Laid-Open No. 2009-077879 or 2009-183583 can be used as the three-way stopcock 6 for bone marrow cell suspension.

In the present first embodiment, the connecting unit 24 for bone marrow cell suspension is exemplified by the three-way stopcock 6 for bone marrow cell suspension, but is not limited to this. Another constitution may be adopted in which the bone marrow fluid storing syringe 21 and the medium storing syringe 22 are selectively inserted to the transporting vessel tube 26 and thereby communicated therewith.

The blood collecting and storing device 3 is constituted mainly of a vascular puncture needle 31, a blood storing vessel 32, and a connecting unit 33 for blood collection.

The vascular puncture needle 31 is not limited as long as the needle can be inserted to the blood vessel of the subject to allow blood to flow therewithin and can be usually used in the medical field.

Figure 3:
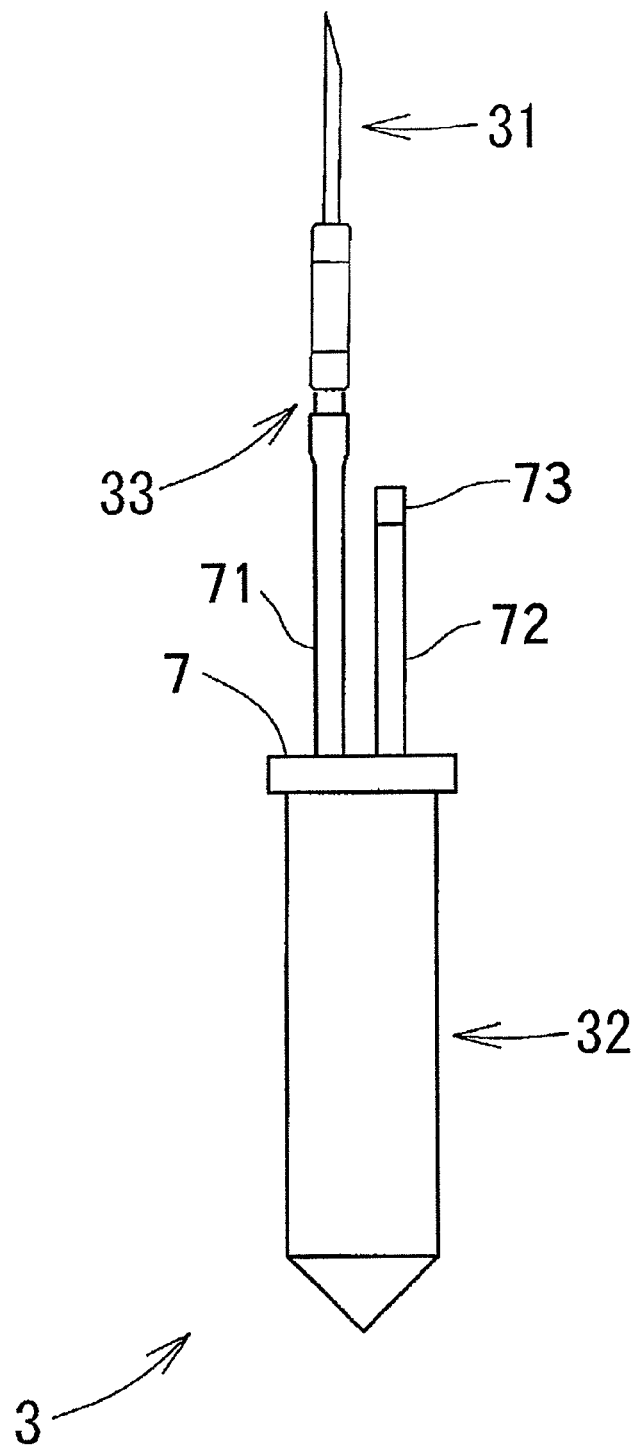
FIG. 3 is a diagram showing a blood collecting and storing device of the first and second embodiments.

The blood storing vessel 32 is not particularly limited as long as the vessel is a liquid-tightly sealable vessel which stores the blood of the subject and is capable of being centrifuged and can be usually used in the medical field. Examples of such constitution can include constitution in which, as shown in FIG. 3, the blood storing vessel 32 permits injection of blood from the vascular puncture needle 31 via the connecting unit 33 for blood collection and can be sealed in a liquid-tight state and centrifuged, and the blood storing vessel 32 has an open upper end to which a storing vessel lid 7 is fastened in a liquid-tightly sealable manner with screws, the storing vessel lid 7 comprising a storing vessel tube 71 and a storing vessel vent 72. The storing vessel tube 71 communicates the connecting unit 33 for blood collection with the interior space of the blood storing vessel 32. The storing vessel vent 72 communicates the interior space of the blood storing vessel 32 with exterior space. The storing vessel vent 72 is provided at its tip with a storing vessel vent filter 73 that prevents bacteria from entering the vent.

The connecting unit 33 for blood collection is not limited as long as the unit is constitutionally or functionally capable of distributing blood and capable of liquid-tightly connecting the vascular puncture needle 31 and the blood storing vessel 32.

Figure 4:
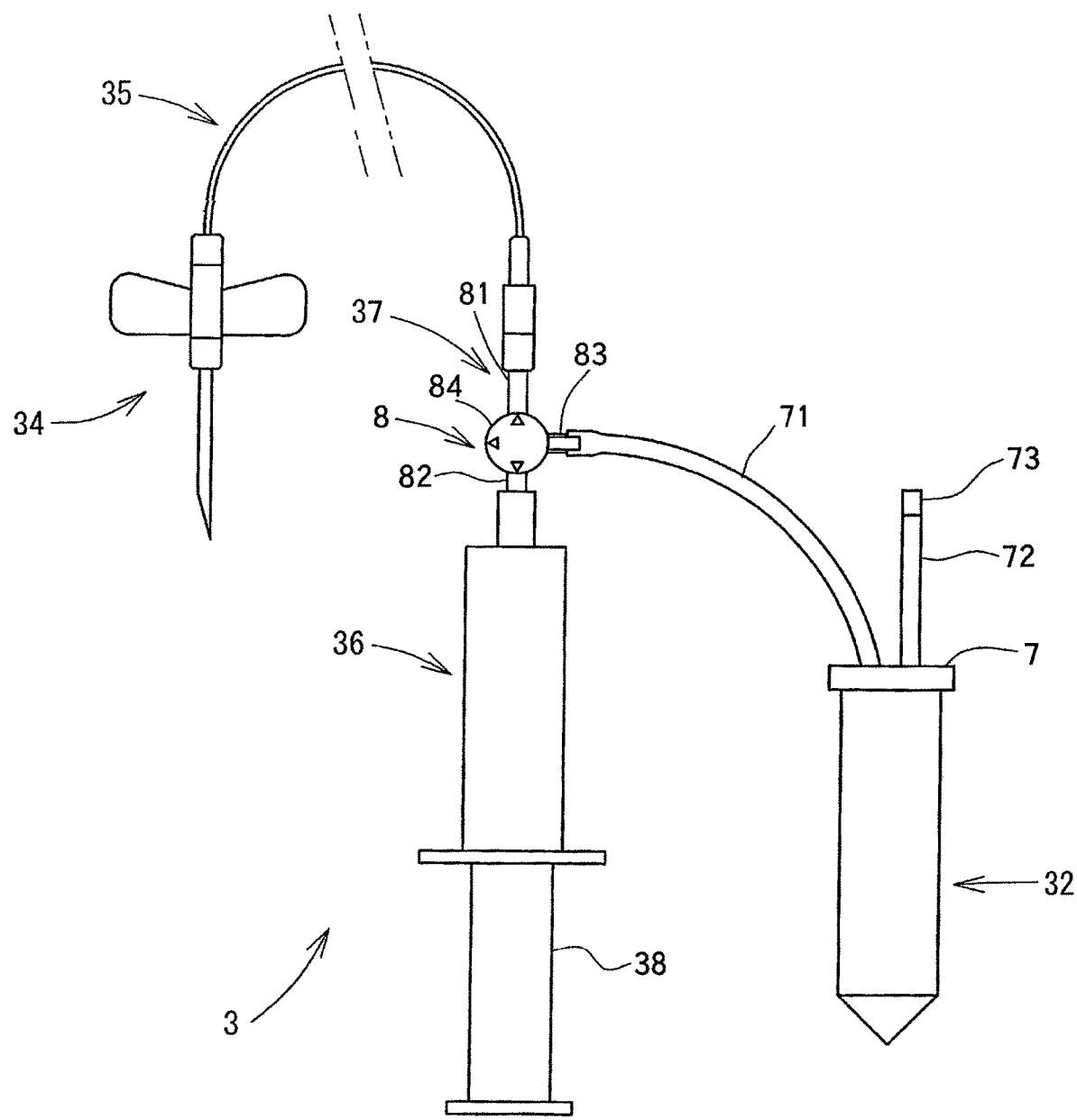
FIG. 4 is a diagram showing a different embodiment of the blood collecting and storing device according to the first and second embodiments.
Figure 5:
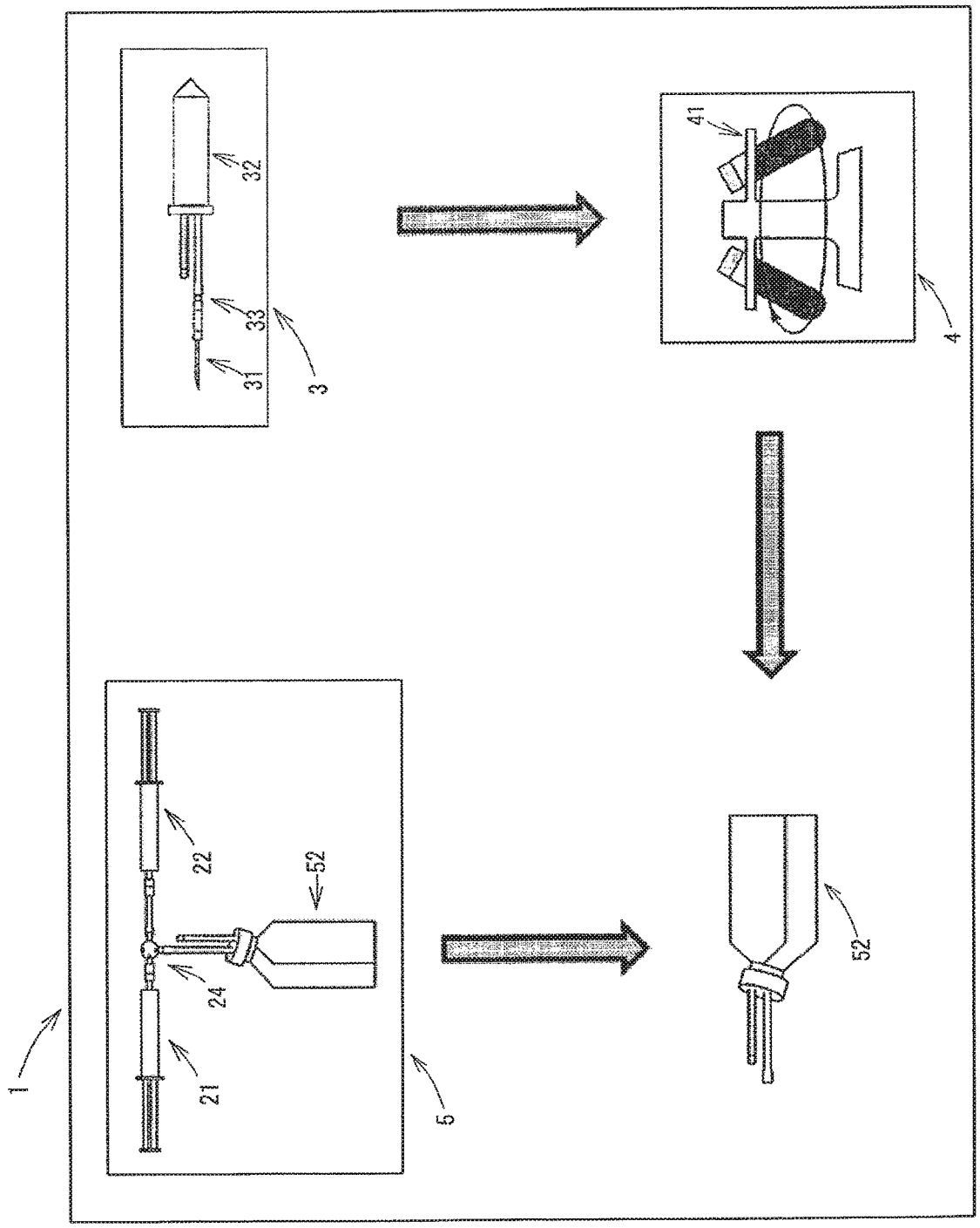
FIG. 5 is a diagram showing the second embodiment of the autoserum-containing bone marrow cell culture system according to the present invention.

Alternatively, in a different embodiment, the blood collecting and storing device 3 is constituted mainly of, as shown in FIG. 4, an indwelling needle 34, an indwelling needle connection tube 35 connected with the indwelling needle 34, a blood storing vessel 32, a syringe 36 for blood collection, and a three-way connecting unit 37 for blood collection. In this constitution of the blood collecting and storing device 3, the same reference numerals will be used to designate the same or similar components as those in the constitution described above, so that the description will be omitted.

The indwelling needle 34 is a blood collection needle capable of maintaining a state inserted to the blood vessel of the subject. The indwelling needle 34 is not particularly limited as long as the needle can be usually used in the medical field. The indwelling needle 34 is preferably a butterfly needle because the butterfly needle can be anchored easily to a limb or the like of the subject. Examples of the butterfly needle include those described in International Publication No. WO2006/123645.

The indwelling needle connection tube 35 is connected at one end with the indwelling needle 34 and connected at the other end with the three-way connecting unit 37 for blood collection. Blood is distributed to the three-way connecting unit 37 for blood collection from the indwelling needle 34 through the indwelling needle connection tube 35. The indwelling needle connection tube 35 is not particularly limited as long as the tube is a medical tube.

The syringe 36 for blood collection is not particularly limited as long as the syringe is capable of collecting, storing blood from the subject and pushing the blood out in a liquid-tight state. Examples thereof can include those usually used in the medical field.

The three-way connecting unit 37 for blood collection is not limited as long as the unit is constitutionally or functionally capable of distributing blood and capable of liquid-tightly connecting the indwelling needle connection tube 35 connected with the indwelling needle 34, the syringe 36 for blood collection, and the blood storing vessel 32. Examples of such constitution can include constitution having, as shown in FIG. 4, a three-way stopcock 8 for blood collection. The three-way stopcock 8 for blood collection has three connecting ports, i.e., a first port 81 for blood collection, a second port 82 for blood collection, and a third port 83 for blood collection, and a cock 84 for blood collection which selectively communicates two of these connecting ports. The cock 84 for blood collection can be turned to change its posture at least to a posture by which the first port 81 for blood collection and the second port 82 for blood collection are communicated with each other, and a posture by which the second port 82 for blood collection and the third port 83 for blood collection are communicated with each other. For example, a stopcock similar to the three-way stopcock 6 for bone marrow cell suspension can be used as the three-way stopcock 8 for blood collection.

In the present first embodiment, the connecting unit 33 for blood collection is exemplified by the constitution that communicates the blood storing vessel 32 with the vascular puncture needle 31 and by the three-way connecting unit 37 for blood collection, but is not limited to them. Alternative constitution may be adopted.

The autoserum acquiring device 4 is constituted of a centrifuging unit 41. The centrifuging unit 41 is not particularly limited as long as the unit is capable of centrifuging the blood storing vessel 32 where the blood of the subject is stored to obtain the serum of the subject. Examples thereof can include centrifuges usually used.

The bone marrow cell culturing device 5 is constituted of a bone marrow cell culture vessel 51. The bone marrow cell culture vessel 51 is not particularly limited as long as the vessel cultures the bone marrow cells after transfer of the bone marrow cell suspension. Examples thereof can include dishes (e.g., plastic or glass Petri dishes), glass plates fixed in vessels, well plates, cell culture sheets, cell culture flasks, and spinner flasks. A rigid vessel is preferred.

Next, the effects of the bone marrow cell suspension storing device 2, the blood collecting and storing device 3, the autoserum acquiring device 4, the bone marrow cell culturing device 5, and the autoserum-containing bone marrow cell culture system 1 comprising these devices according to the present first embodiment, an autoserum-containing bone marrow cell culture method, and a method for producing a medicinal composition comprising autoserum-containing cultured bone marrow cells as an active ingredient will be described.

In the bone marrow cell suspension storing device 2, a bone marrow fluid collected from the subject is liquid-tightly mixed with a medium to prepare an anticoagulated bone marrow cell suspension, which is then transported to a cell processing center (CPC), which is the location of cell culture. Hereinafter, the process will be described in detail.

The bone marrow fluid collected from the subject is stored in the bone marrow fluid storing syringe 21. Although the bone marrow fluid is collected from the subject, description about the approach of collecting the bone marrow fluid from the subject will be omitted. As shown in FIG. 2, the bone marrow fluid storing syringe 21 where the bone marrow fluid containing bone marrow cells collected from the subject is stored is connected, at the site of collection, to the first port 61 for suspension of the three-way stopcock 6 for bone marrow cell suspension serving as the connecting unit 24 for bone marrow cell suspension. Then, the cock 64 for suspension is turned to achieve the state in which the first port 61 for suspension and the second port 62 for suspension are communicated with each other. Subsequently, the bone marrow fluid stored in the bone marrow fluid storing syringe 21 is pushed out of the bone marrow fluid storing syringe 21 so that the bone marrow fluid is injected from the first port 61 for suspension through the second port 62 for suspension and the transporting vessel tube 26 to the bone marrow cell suspension transporting vessel 23 while air is discharged from the interior space of the bone marrow cell suspension transporting vessel 23 through the transporting vessel vent 27.

The medium storing syringe 22 is connected to the third port 63 for suspension before the connection of the bone marrow fluid storing syringe 21 to the first port 61 for suspension. Then, the cock 64 for suspension is turned to shift the state to that in which the second port 62 for suspension and the third port 63 for suspension are communicated with each other. Subsequently, a medium stored in the medium storing syringe 22 is pushed, in an amount appropriate for the amount of the bone marrow fluid stored in the bone marrow fluid storing syringe 21, out of the medium storing syringe 22 so that the medium is injected from the third port 63 for suspension through the second port 62 for suspension and the transporting vessel tube 26 to the bone marrow cell suspension transporting vessel 23 while air is discharged from the interior space of the bone marrow cell suspension transporting vessel 23 through the transporting vessel vent 27. As a result, in the bone marrow cell suspension transporting vessel 23, the bone marrow fluid collected from the subject and the medium in an amount appropriate for the amount of this bone marrow fluid are liquid-tightly mixed to prepare an anticoagulated bone marrow cell suspension.

In the aspect described above, the bone marrow fluid storing syringe 21 is connected to the first port 61 for suspension after the connection of the medium storing syringe to the third port 63 for suspension. The order in which these components are connected is not particularly limited. The medium storing syringe may be connected to the third port 63 for suspension after the connection of the bone marrow fluid storing syringe 21 to the first port 61 for suspension, or otherwise, these syringes may be connected simultaneously. The amount of the medium appropriate for the amount of the bone marrow fluid is preferably 1.5 times to 6 times the amount of the bone marrow fluid stored in the bone marrow fluid storing syringe 21. In this regard, at least one of the medium storing syringe 22, the bone marrow fluid storing syringe 21, and the bone marrow cell suspension transporting vessel 23 are preferably graduated in order to visually measure the volume of the contents.

Then, the transporting vessel tube 26 is liquid-tightly sealed with a heat sealer or clip and then cut between the sealed portion and the second port 62 for suspension to separate the bone marrow cell suspension transporting vessel 23 from the bone marrow fluid storing syringe 21, the medium storing syringe 22, and the connecting unit 24 for bone marrow cell suspension. The bone marrow cell suspension stored in the bone marrow cell suspension transporting vessel 23 is transported in a suspended state to CPC.

Meanwhile, in the blood collecting and storing device 3, the blood of the subject is stored in the blood storing vessel 32. Hereinafter, the process will be described in detail.

The vascular puncture needle 31 is inserted to the blood vessel of the subject to collect blood. The collected blood is injected to the blood storing vessel 32 through the connecting unit 33 for blood collection and the storing vessel tube 71 while air is discharged from the interior space of the blood storing vessel 32 through the storing vessel vent 72. As a result, the collected blood is liquid-tightly stored in the blood storing vessel 32.

Then, the storing vessel tube 71 is liquid-tightly sealed with a heat sealer or clip and then cut between the sealed portion and the connecting unit 33 for blood collection to separate the blood storing vessel 32 where the blood of the subject is stored from the vascular puncture needle 31 and the connecting unit 33 for blood collection.

Alternatively, in the case of adopting the different aspect of the blood collecting and storing device 3, the indwelling needle 34 is indwelled in a state inserted to the blood vessel of the subject. This eliminates the need to repetitively insert the blood collection needle to the subject for obtaining the desired amount of blood. As shown in FIG. 4, the first port 81 for blood collection of the three-way stopcock 8 for blood collection is connected to the indwelling needle connection tube 35 connected with the indwelling needle 34. As a result, blood can be injected from the indwelling needle 34 to the three-way connecting unit 37 for blood collection. The cock 84 for blood collection of the three-way stopcock 8 for blood collection is turned to achieve the state in which the first port 81 for blood collection and the second port 82 for blood collection are communicated with each other. In this state, a plunger 38 for blood collection of the syringe 36 for blood collection is pulled to collect blood from the subject. This blood collection is continued by the active operation of continuing to pull the plunger 38 for blood collection by the operator.

Once the interior of the syringe 36 for blood collection is filled with the blood of the subject, the operation with the plunger 38 for blood collection is suspended. Then, the cock 84 for blood collection of the three-way stopcock 8 for blood collection is turned to shift the state to that in which the second port 82 for blood collection and the third port 83 for blood collection are communicated with each other. The plunger 38 for blood collection is operated again. Specifically, the plunger 38 for blood collection is pushed to eject blood from the syringe 36 for blood collection. This ejected blood is injected to the blood storing vessel 32 through the three-way stopcock 8 for blood collection. Once the blood in the syringe 36 for blood collection is completely injected to the blood storing vessel 32, the operation with the plunger 38 for blood collection is terminated. After the injection of the blood to the blood storing vessel 32, the storing vessel tube 71 is liquid-tightly sealed with a heat sealer or clip and then cut between the sealed portion and the third port 83 for blood collection to separate the blood storing vessel 32 where the blood of the subject is stored from the indwelling needle 34, the indwelling needle connection tube 35, the syringe 36 for blood collection, and the three-way connecting unit 37 for blood collection.

Subsequently, in the autoserum acquiring device 4, serum is obtained from the blood of the subject. The blood storing vessel 32 where the blood of the subject is stored is centrifuged in the centrifuging unit 41. Then, the supernatant is collected to obtain the serum of the subject.

The bone marrow cells contained in the bone marrow cell suspension is cultured in the bone marrow cell culturing device 5. The culture supernatant containing floating cells is removed from the bone marrow cell culture vessel 51. Then, the obtained serum of the subject and a fresh medium are added to the bone marrow cell culture vessel 51 to further culture the cells. Hereinafter, the process will be described in detail.

The bone marrow cell suspension transported to CPC is transferred to the bone marrow cell culture vessel 51. The bone marrow cells contained in this bone marrow cell suspension are cultured for a predetermined culture period. The predetermined culture period is preferably 4 days to 7 days.

After the culture, the culture supernatant containing floating cells is removed from the bone marrow cell culture vessel 51. The obtained serum of the subject and a fresh medium are added to the bone marrow cell culture vessel 51 to further culture the cells.

The bone marrow cells may be cultured for the predetermined culture period by adding at least one of a fresh medium and the obtained serum of the subject when the bone marrow cell suspension transported to CPC is transferred to the bone marrow cell culture vessel 51. In the case of adding the fresh medium without adding the serum of the subject, this addition is preferably performed so that the total amount of the media mixed with the bone marrow fluid, i.e., the total sum of the amount of the medium mixed with the bone marrow fluid at the site of bone marrow fluid collection and the amount of the added fresh medium, is 4 times to 80 times the amount of the bone marrow fluid stored in the bone marrow fluid storing syringe 21. Alternatively, in the case of adding only the obtained serum of the subject, this addition is preferably performed so that the total amount of the medium mixed with the bone marrow fluid and the obtained serum of the subject, i.e., the total sum of the amount of the medium mixed with the bone marrow fluid at the site of bone marrow fluid collection and the amount of the added obtained serum of the subject, is 4 times to 80 times the amount of the bone marrow fluid stored in the bone marrow fluid storing syringe 21. Alternatively in the case of adding both the fresh medium and the obtained serum of the subject, this addition is preferably performed so that the total amount of the media mixed with the bone marrow fluid and the obtained serum of the subject, i.e., the total sum of the amount of the medium mixed with the bone marrow fluid at the site of bone marrow fluid collection, the amount of the added fresh medium, and the amount of the added obtained serum of the subject, is 4 times to 80 times the amount of the bone marrow fluid stored in the bone marrow fluid storing syringe 21.

Figure 7:
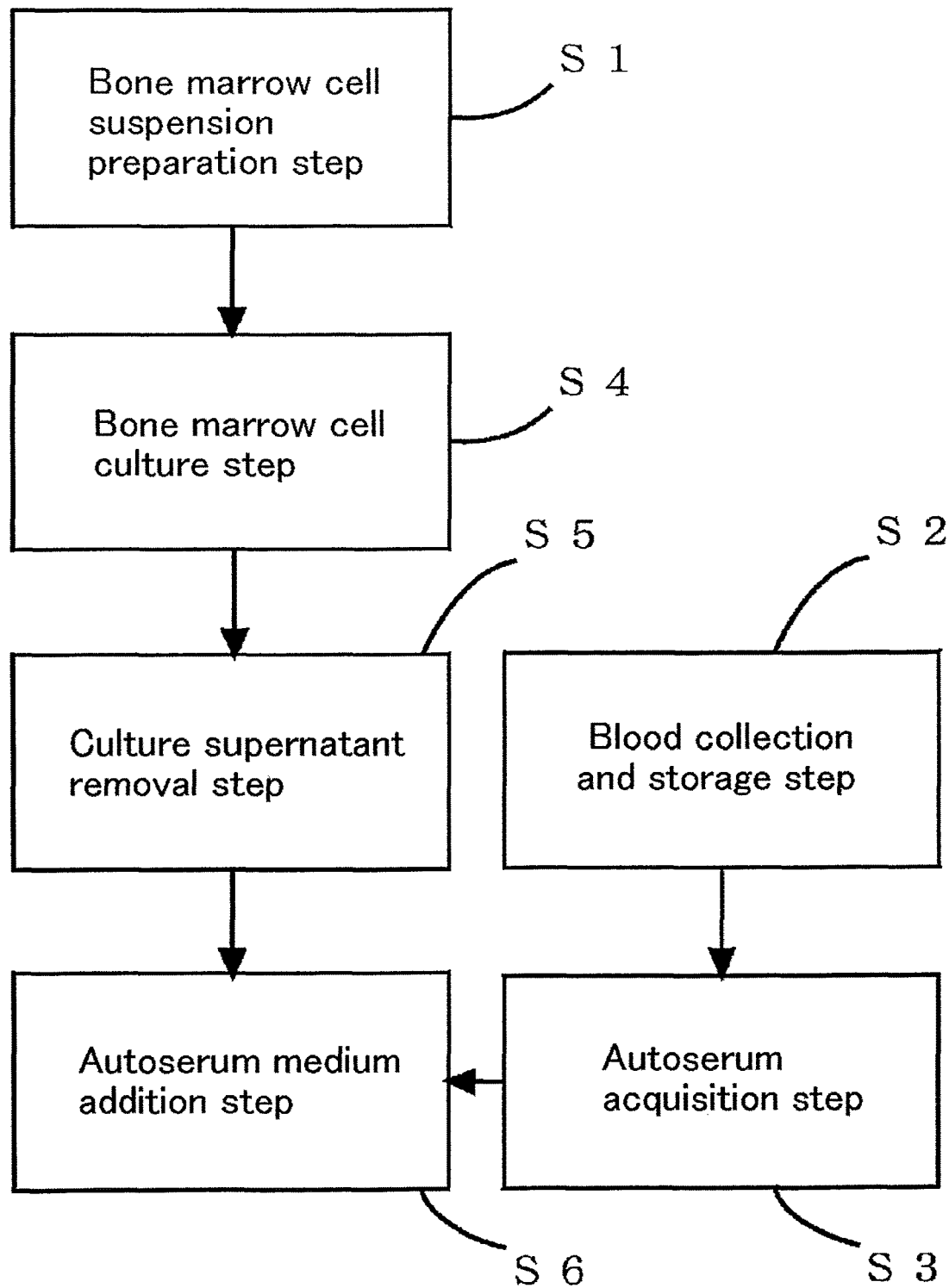
FIG. 7 is a flow chart showing the first embodiment of the autoserum-containing bone marrow cell culture method according to the present invention.

Next, the autoserum-containing bone marrow cell culture method according to the present first embodiment comprises, as shown in FIG. 7, bone marrow cell suspension preparation step S1, blood collection and storage step S2, autoserum acquisition step S3, bone marrow cell culture step S4, culture supernatant removal step S5, and autoserum medium addition step S6, wherein: a bone marrow fluid is transferred at the site of collection from the bone marrow fluid storing syringe 21 to the bone marrow cell suspension transporting vessel 23 and then anticoagulated by mixing with a medium; the resulting bone marrow cell suspension is transported in a suspended state while stored in the bone marrow cell suspension transporting vessel 23, and then transferred to the bone marrow cell culture vessel 51 at CPC to start culture; after a lapse of a predetermined culture period, the culture supernatant containing floating cells is removed; and a fresh medium and the serum of the subject are added into the bone marrow cell culture vessel 51 to perform further culture. In the invention-specifying matters of the autoserum-containing bone marrow cell culture method according to the present first embodiment, the same reference numerals will be used to designate the same or similar components as those in each constitution described above in the autoserum-containing bone marrow cell culture system 1 according to the present first embodiment, so that the description will be omitted.

The bone marrow cell suspension preparation step S1 is a step that is performed in the bone marrow cell suspension storing device 2. In this step, a bone marrow fluid containing bone marrow cells collected from the subject is anticoagulated by mixing with a medium in an amount appropriate for the amount of the bone marrow fluid in a liquid-tight state at the site of collection of the bone marrow fluid immediately after the collection to prepare an anticoagulant-free bone marrow cell suspension. The amount appropriate for the amount of the bone marrow fluid is preferably 1.5 times to 6 times the amount of the bone marrow fluid.

In this context, the "anticoagulant" described in the present invention refers to a drug or agent that prevents the coagulation of biogenic substances such as blood components and prevents clot formation, for example, heparin (e.g., heparin sodium and heparin calcium), low-molecular-weight heparin (e.g., dalteparin sodium, parnaparin sodium, and reviparin sodium), nafamostat mesilate, gabexate mesilate, citric acid, citrate-phosphate-dextrose (CPD) solution, acid-citrate-dextrose-A (ACD-A) solution, warfarin, coumarin, dicumarol, phenprocoumon, acenocoumarol, ethyl biscoumacetate, or indanedione derivatives and is meant to exclude something, such as the cellular medium used in the present invention, which neither originally prevents the coagulation of biogenic substances such as blood components nor prevents clot formation as a drug or agent, though it suppresses coagulation in the event. Specifically, the terms "anticoagulant", "anticoagulant except for a cellular medium", "anticoagulant except for a medium" may be used interchangeably.

The blood collection and storage step S2 is a step that is performed in the blood collecting and storing device 3. In this step, blood collected from the subject without addition of an anticoagulant is stored in a liquid-tight state in the blood storing vessel 32 capable of being centrifuged. The blood storing vessel 32 is preferably a rigid vessel capable of being centrifuged.

The autoserum acquisition step S3 is a step that is performed in the autoserum acquiring device 4. In this step, the blood storing vessel 32 where the blood of the subject is stored is centrifuged to obtain the serum of the subject.

The bone marrow cell culture step S4 is a step that is performed in the bone marrow cell culturing device 5. In this step, the bone marrow cells contained in the prepared bone marrow cell suspension are cultured in the bone marrow cell culture vessel 51. In the bone marrow cell culture step S4, the culture of the bone marrow cells is preferably static culture. As described above, the bone marrow cells contained in the bone marrow cell suspension are preferably cultured for 4 days to 7 days.

The culture supernatant removal step S5 is a step that is performed in the bone marrow cell culturing device 5. In this step, the culture supernatant containing floating cells is removed from the bone marrow cell culture vessel 51 with the thus-cultured bone marrow cells attached thereto.

The autoserum medium addition step S6 is a step that is performed in the bone marrow cell culturing device 5. In this step, the obtained serum of the subject and a medium are added to the bone marrow cell culture vessel 51 with the bone marrow cells attached thereto.

Figure 8:
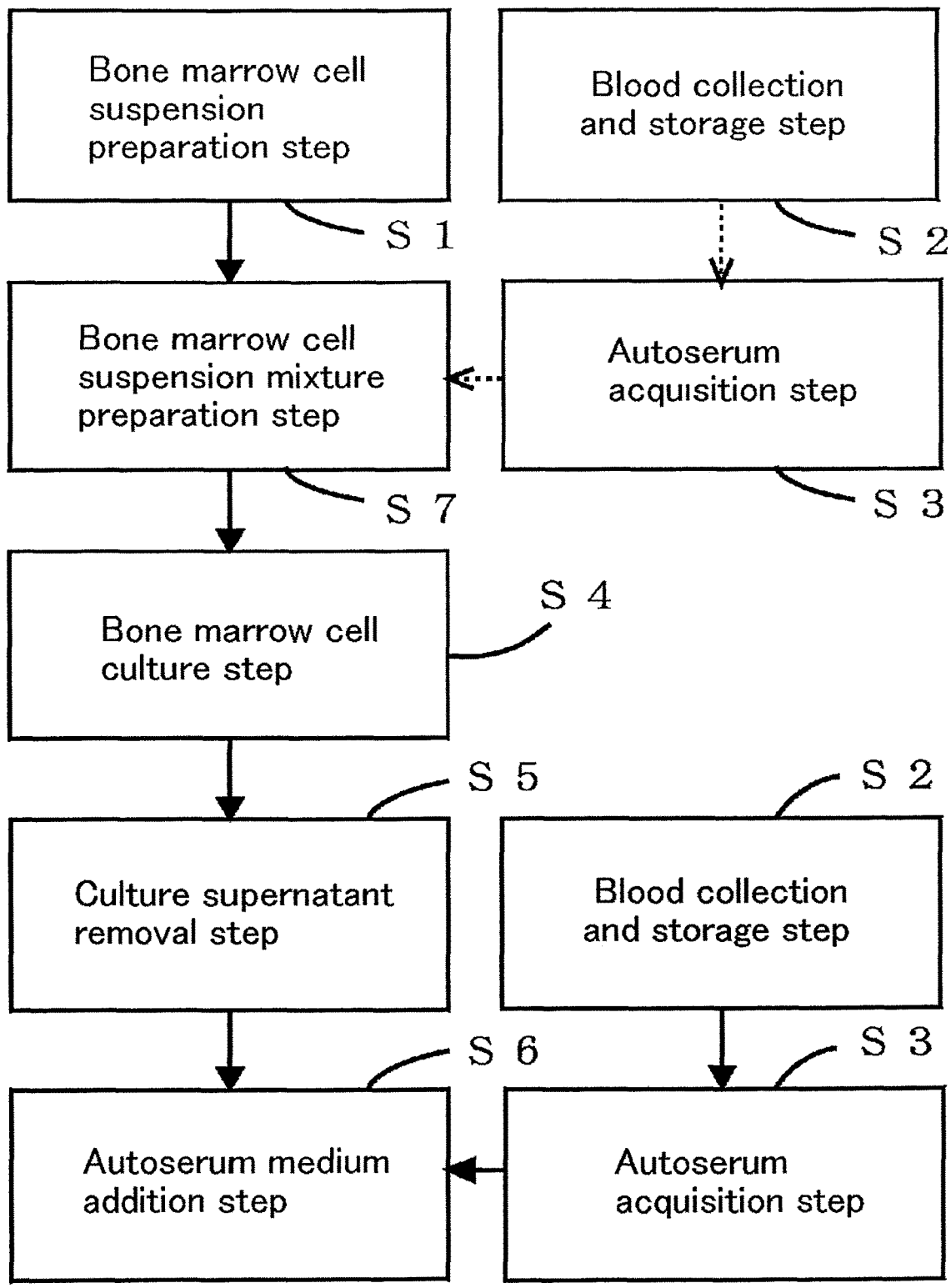
FIG. 8 is a flow chart showing an aspect of the autoserum-containing bone marrow cell culture method according to the first embodiment, further having bone marrow cell suspension mixture preparation step S7. In the diagram, the dashed arrows represent that selection is possible.

As shown in FIG. 8, the autoserum-containing bone marrow cell culture method according to the present first embodiment may further comprise bone marrow cell suspension mixture preparation step S7 described later. In this case, the "bone marrow cell suspension" in the bone marrow cell culture step S4 shall be replaced by a "bone marrow cell suspension mixture".

The bone marrow cell suspension mixture preparation step S7 is a step that is performed in the bone marrow cell culturing device 5. In this step, the prepared bone marrow cell suspension is mixed with a medium and/or the obtained serum of the subject to prepare a bone marrow cell suspension mixture. Specifically, in this step, at least one of a fresh medium and the obtained serum of the subject are added when the bone marrow cell suspension is transferred to the bone marrow cell culture vessel 51, to prepare a bone marrow cell suspension mixture. In the case of adding the fresh medium without adding the serum of the subject, this addition is preferably performed so that the total amount of the media in the bone marrow cell suspension mixture, i.e., the total sum of the amount of the medium mixed with the bone marrow fluid in the bone marrow cell suspension preparation step S1 and the amount of the fresh medium added in the bone marrow cell suspension mixture preparation step S7, is 4 times to 80 times the amount of the bone marrow fluid containing bone marrow cells collected from the subject in the bone marrow cell suspension preparation step S1. Alternatively, in the case of adding only the obtained serum of the subject, this addition is preferably performed so that the total amount of the medium mixed with the bone marrow fluid and the obtained serum of the subject, i.e., the total sum of the amount of the medium mixed with the bone marrow fluid in the bone marrow cell suspension preparation step S1 and the amount of the obtained serum of the subject added in the bone marrow cell suspension mixture preparation step S7, is 4 times to 80 times the amount of the bone marrow fluid containing bone marrow cells collected from the subject in the bone marrow cell suspension preparation step S1. Alternatively in the case of adding both the fresh medium and the obtained serum of the subject, this addition is preferably performed so that the total amount of the media mixed with the bone marrow fluid and the serum, i.e., the total sum of the amount of the medium mixed with the bone marrow fluid in the bone marrow cell suspension preparation step S1, the amount of the fresh medium added in the bone marrow cell suspension mixture preparation step S7, and the amount of the obtained serum of the subject added in the bone marrow cell suspension mixture preparation step S7, is 4 times to 80 times the amount of the bone marrow fluid containing bone marrow cells collected from the subject in the bone marrow cell suspension preparation step S1.

Figure 10:
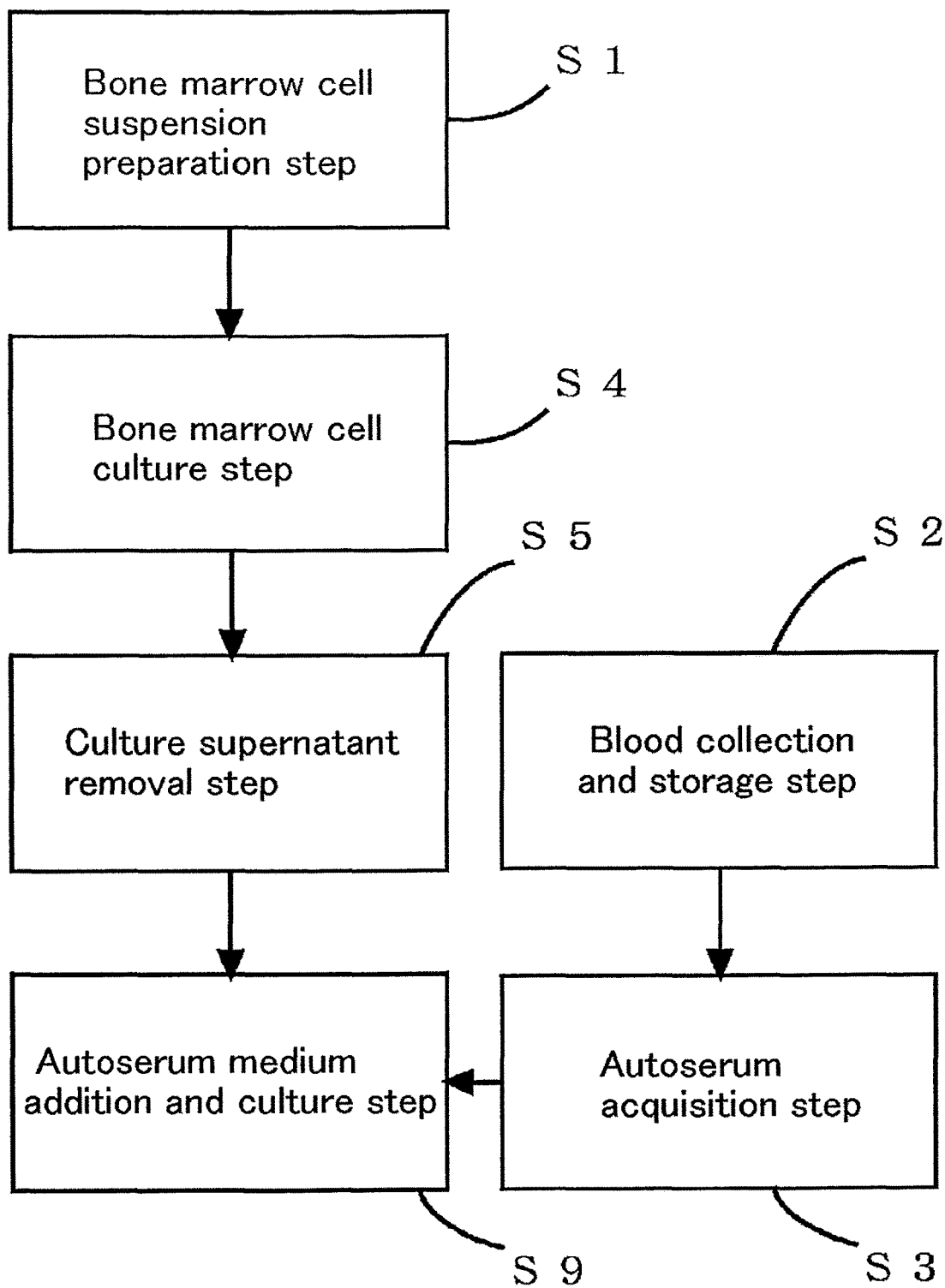
FIG. 10 is a flow chart showing the first embodiment of the method for producing a medicinal composition comprising autoserum-containing cultured bone marrow cells as an active ingredient according to the present invention.

Next, the method for producing a medicinal composition comprising autoserum-containing cultured bone marrow cells as an active ingredient according to the present first embodiment comprises, as shown in FIG. 10, bone marrow cell suspension preparation step S1, blood collection and storage step S2, autoserum acquisition step S3, bone marrow cell culture step S4, culture supernatant removal step S5, and autoserum medium addition and culture step S9, wherein: a bone marrow fluid is transferred at the site of collection from the bone marrow fluid storing syringe 21 to the bone marrow cell suspension transporting vessel 23 and then anticoagulated by mixing with a medium; the resulting bone marrow cell suspension is transported in a suspended state while stored in the bone marrow cell suspension transporting vessel 23, and then transferred to the bone marrow cell culture vessel 51 at CPC to start culture; after a lapse of a predetermined culture period, the culture supernatant containing floating cells is removed; and a fresh medium and the serum of the subject are added into the bone marrow cell culture vessel 51 to perform further culture. In the invention-specifying matters of the method for producing a medicinal composition comprising autoserum-containing cultured bone marrow cells as an active ingredient according to the present first embodiment, the same reference numerals will be used to designate the same or similar components or steps as those in each constitution and each invention-specifying matter described above in the autoserum-containing bone marrow cell culture system 1 and the autoserum-containing bone marrow cell culture method according to the present first embodiment, so that the description will be omitted.

The autoserum medium addition and culture step S9 is a step that is performed in the bone marrow cell culturing device 5. In this step, the obtained serum of the subject and a medium are added to the bone marrow cell culture vessel 51 with the bone marrow cells attached thereto to perform further culture.

Figure 11:
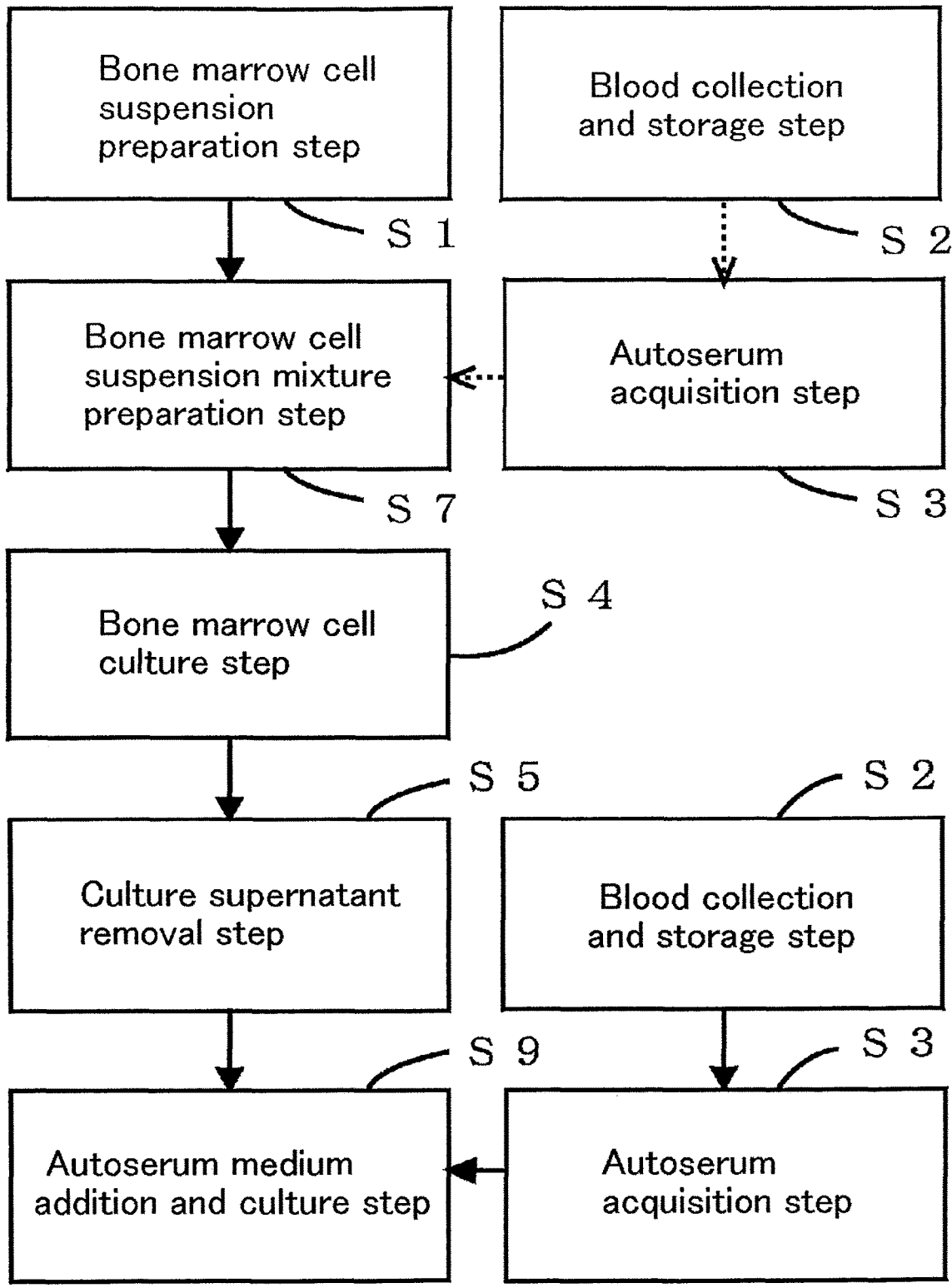
FIG. 11 is a flow chart showing an aspect of the method for producing a medicinal composition comprising autoserum-containing cultured bone marrow cells as an active ingredient according to the first embodiment, further having bone marrow cell suspension mixture preparation step S7. In the diagram, the dashed arrows represent that selection is possible.

As shown in FIG. 11, the method for producing a medicinal composition comprising autoserum-containing cultured bone marrow cells as an active ingredient according to the present first embodiment may further have the bone marrow cell suspension mixture preparation step S7 described above. In this case, the "bone marrow cell suspension" in the bone marrow cell culture step S4 shall be replaced by a "bone marrow cell suspension mixture".

The bone marrow cell suspension storing device 2, the blood collecting and storing device 3, the autoserum acquiring device 4, the bone marrow cell culturing device 5, and the autoserum-containing bone marrow cell culture system 1 comprising these devices according to the present first embodiment, the autoserum-containing bone marrow cell culture method, and the method for producing a medicinal composition comprising autoserum-containing cultured bone marrow cells as an active ingredient produce the following effects:

1. The bone marrow cells contained in the bone marrow fluid collected from the subject can be anticoagulated cleanly and conveniently in a liquid-tight state to efficiently obtain the bone marrow cells of interest.
2. The blood of the subject can be stored cleanly and conveniently in a liquid-tight state, and the serum thereof can be obtained efficiently.
3. The bone marrow cells of the subject can be cultured using the autoserum and thereby grown efficiently, and the resulting bone marrow cells can be used in regenerative medicine.
4. The bone marrow cells contained in the bone marrow fluid collected from the subject can be grown conveniently and reliably even when the amount of the cells is small, and the resulting bone marrow cells can be used in regenerative medicine.

Next, the second embodiment of the autoserum-containing bone marrow cell culture system 1 according to the present invention will be described in detail. In the second embodiment, an autoserum-containing bone marrow cell culture system 1 according to the present invention is an autoserum-containing bone marrow cell culture system for culturing bone marrow cells collected from a subject without use of an anticoagulant with the serum of the subject, wherein: a bone marrow fluid containing bone marrow cells collected from the subject is transferred at the site of collection from a bone marrow fluid storing syringe 21 where the bone marrow fluid is stored to a bone marrow cell culturing and transporting vessel 52 which is a liquid-tightly sealable rigid vessel that stores an anticoagulated bone marrow cell suspension obtained by mixing the bone marrow fluid with a medium and starts culture of the bone marrow cells, and then mixed with the medium to perform anticoagulation while starting culture of the bone marrow cells; the resulting bone marrow cell suspension is transported in a cultured state while stored in the bone marrow cell culturing and transporting vessel 52; after a lapse of a predetermined culture period, the culture supernatant is removed; and at the location of cell culture, a medium and the serum of the subject are added into the bone marrow cell culturing and transporting vessel 52 to perform further culture.

In the present second embodiment, the autoserum-containing bone marrow cell culture system 1 according to the present invention preferably comprises at least one of a blood collecting and storing device 3, an autoserum acquiring device 4, and a bone marrow cell culturing device 5 and more preferably comprises all of these devices. In this constitution of the autoserum-containing bone marrow cell culture system 1 according to the present second embodiment, the same reference numerals will be used to designate the same or similar components as those in each constitution according to the first embodiment described above, so that the description will be omitted.

The bone marrow cell culturing device 5 according to the present second embodiment is constituted mainly of a bone marrow fluid storing syringe 21, a medium storing syringe 22, a bone marrow cell culturing and transporting vessel 52, and a connecting unit 24 for bone marrow cell suspension.

Figure 6:
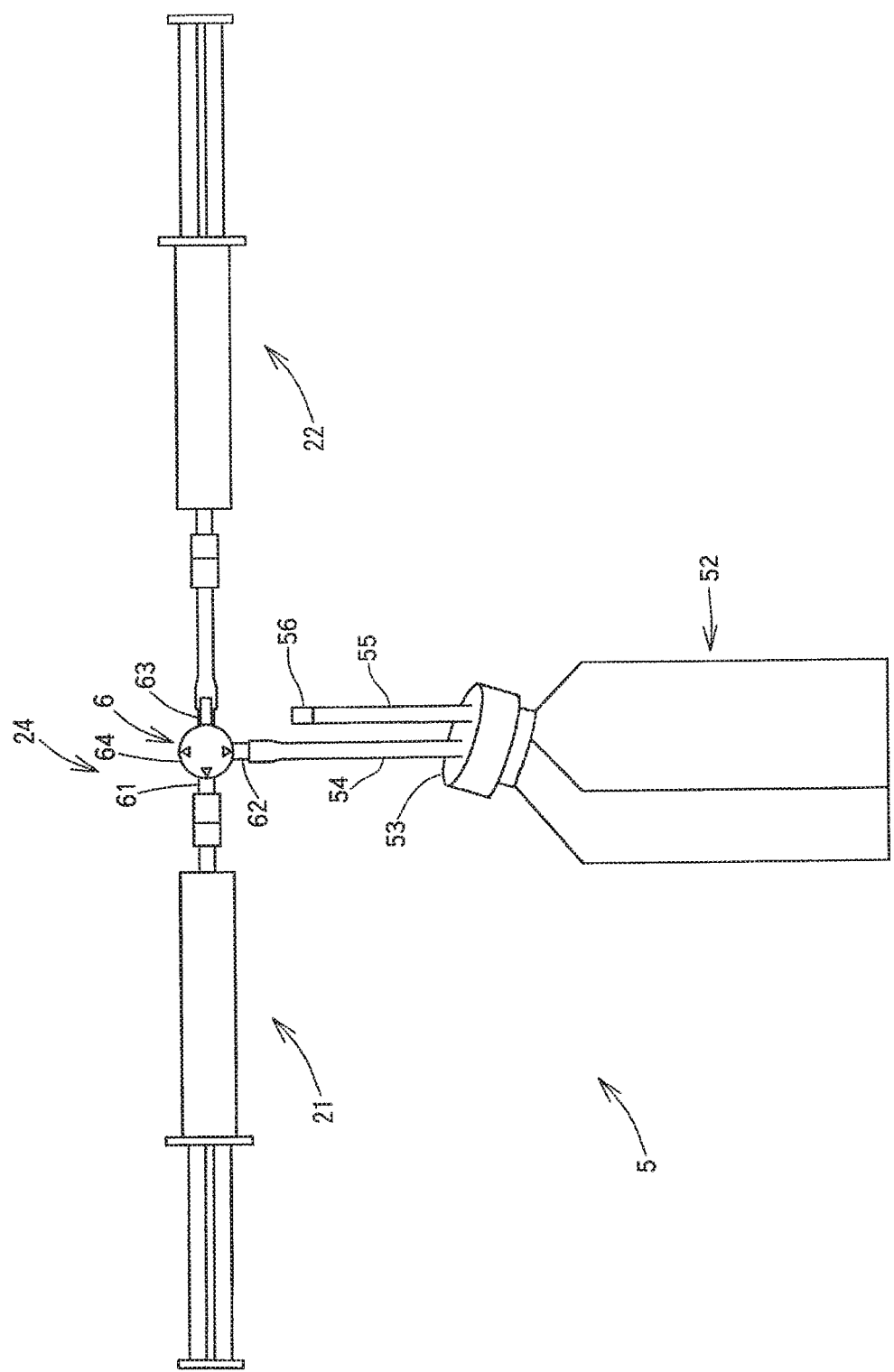
FIG. 6 is a diagram showing a bone marrow cell culturing device according to the second embodiment.

The bone marrow cell culturing and transporting vessel 52 is not particularly limited as long as the vessel is a liquid-tightly sealable rigid vessel that is capable of storing an anticoagulated bone marrow cell suspension obtained by mixing the bone marrow fluid with the medium and capable of culturing the bone marrow cells. Examples of such constitution can include constitution in which, as shown in FIG. 6, the bone marrow cell culturing and transporting vessel 52 has an open upper end to which a culturing and transporting vessel lid 53 is fastened in a liquid-tightly sealable manner with screws, the culturing and transporting vessel lid 53 comprising a culturing and transporting vessel tube 54 and a culturing and transporting vessel vent 55. The culturing and transporting vessel tube 54 penetrates the culturing and transporting vessel lid 53 to communicate the connecting unit 24 for bone marrow cell suspension with the interior space of the bone marrow cell culturing and transporting vessel 52. The culturing and transporting vessel vent 55 penetrates the culturing and transporting vessel lid 53 to communicate the interior space of the bone marrow cell culturing and transporting vessel 52 with exterior space. The culturing and transporting vessel vent 55 is provided at its tip with a culturing and transporting vessel vent filter 56 that prevents bacteria from entering the vent. Those similar to a material for the transporting vessel tube 26 and the transporting vessel vent filter 28 can be used as a material constituting the culturing and transporting vessel tube 54 and the culturing and transporting vessel vent filter 56, respectively.

In the present second embodiment, the connecting unit 24 for bone marrow cell suspension is not limited as long as the unit is constitutionally or functionally capable of distributing the bone marrow fluid and the medium and capable of liquid-tightly connecting the bone marrow fluid storing syringe 21, the medium storing syringe 22, and the bone marrow cell culturing and transporting vessel 52. Examples of such constitution can include constitution having, as shown in FIG. 6, a three-way stopcock 6 for bone marrow cell suspension. The constitution of the three-way stopcock 6 for bone marrow cell suspension according to the present second embodiment is similar to that of the present first embodiment.

Next, the effects of the bone marrow cell culturing device 5, the blood collecting and storing device 3, the autoserum acquiring device 4, and the autoserum-containing bone marrow cell culture system 1 comprising these devices according to the present second embodiment, an autoserum-containing bone marrow cell culture method, and a method for producing a medicinal composition comprising autoserum-containing cultured bone marrow cells as an active ingredient will be described.

In the bone marrow cell culturing device 5, a bone marrow fluid collected from the subject is liquid-tightly mixed with a medium to prepare an anticoagulated bone marrow cell suspension, which is then transported to CPC while the bone marrow cells contained therein are cultured. Hereinafter, the process will be described in detail.

The bone marrow cell suspension prepared by anticoagulation is stored in the bone marrow cell culturing and transporting vessel 52 in a way similar to the storage of the bone marrow cell suspension in the bone marrow cell suspension transporting vessel 23 according to the first embodiment. In the present second embodiment, the bone marrow cell culturing and transporting vessel 52 has constitution in which cultured bone marrow cells can be attached thereto from the start of culture. Thus, a bone marrow cell suspension is prepared while culture of the bone marrow cells contained therein is started so that the cultured bone marrow cells are attached to the bone marrow cell culturing and transporting vessel 52.

Specifically, the bone marrow cell culturing and transporting vessel 52 is not particularly limited as long as the vessel permits attachment of the cultured bone marrow cells from the start of culture. A cell culture flask is preferred. In the second embodiment, the amount of the medium stored in the medium storing syringe 22 is preferably 2 times to 4 times the amount of the bone marrow fluid stored in the bone marrow fluid storing syringe 21.

The bone marrow cells stored in the bone marrow cell culturing and transporting vessel 52 are transported in a cultured state to CPC. After a lapse of a predetermined culture period, the culture supernatant containing floating cells are removed from the bone marrow cell culturing and transporting vessel 52. Then, the autoserum of the subject and a fresh medium are added to the bone marrow cell culturing and transporting vessel 52 to perform further culture. The blood collecting and storing device 3 and the autoserum acquiring device 4 according to the present second embodiment have the same effects as in the first embodiment. The culture of the bone marrow cells after the transport in a cultured state to CPC is preferably static culture. The predetermined culture period is preferably 4 days to 7 days.

Figure 9:
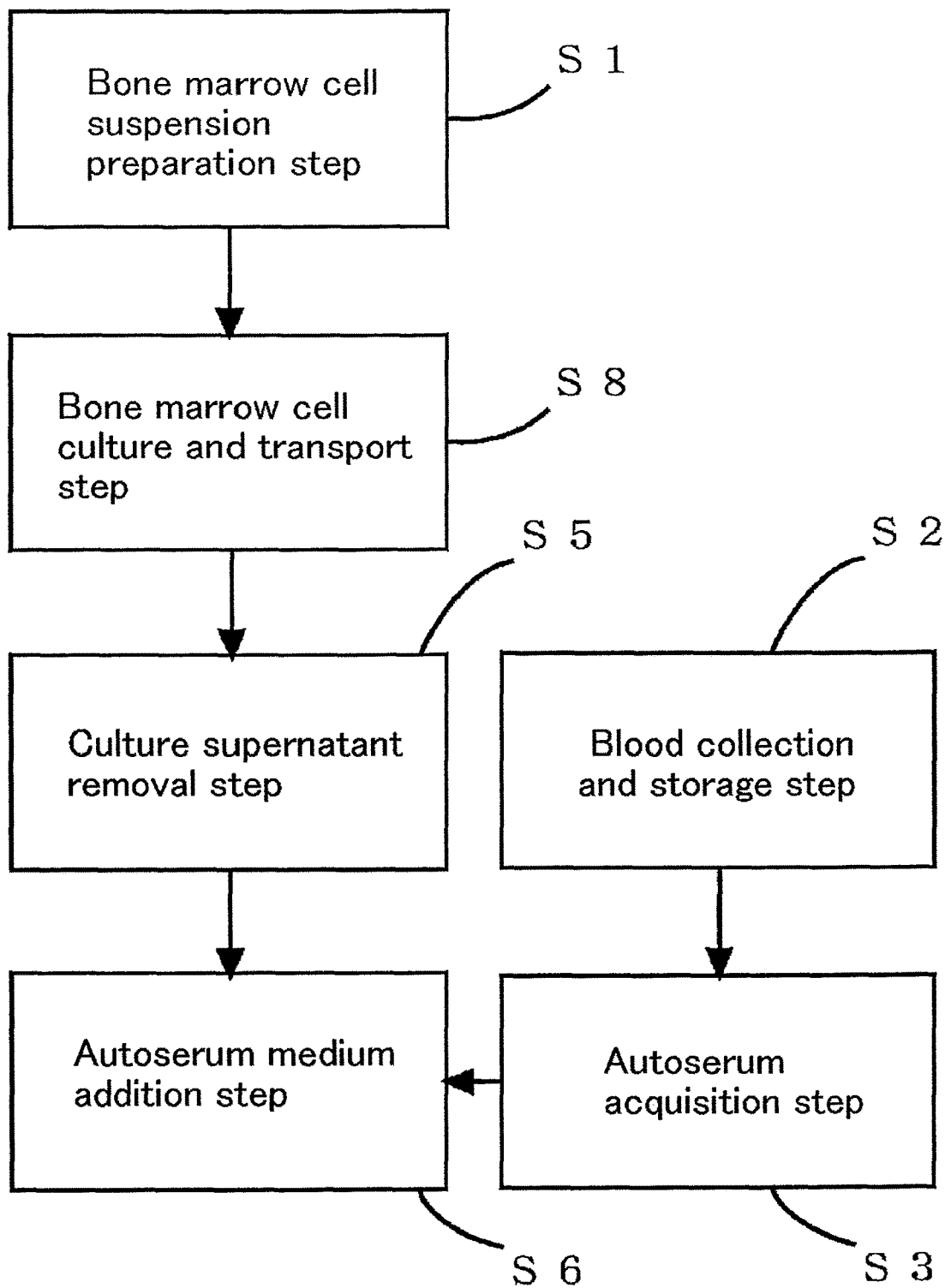
FIG. 9 is a flow chart showing the second embodiment of the autoserum-containing bone marrow cell culture method according to the present invention.

Next, the autoserum-containing bone marrow cell culture method according to the present second embodiment is a method for directly culturing bone marrow cells collected from a subject without use of an anticoagulant and then further culturing the resulting cells using the serum of the subject. Specifically, as shown in FIG. 9, the method comprises bone marrow cell suspension preparation step S1, bone marrow cell culture and transport step S8, blood collection and storage step S2, autoserum acquisition step S3, culture supernatant removal step S5, and autoserum medium addition step S6, wherein: a bone marrow fluid is transferred at the site of collection from the bone marrow fluid storing syringe 21 to the bone marrow cell culturing and transporting vessel 52 and then mixed with a medium to perform anticoagulation while starting culture of the bone marrow cells; the resulting bone marrow cell suspension is transported in a cultured state while stored in the bone marrow cell culturing and transporting vessel 52; after a lapse of a predetermined culture period, the culture supernatant containing floating cells is removed; and at CPC, a fresh medium and the serum of the subject are added into the bone marrow cell culturing and transporting vessel 52 to perform further culture. In the invention-specifying matters of the autoserum-containing bone marrow cell culture method according to the present second embodiment, the same reference numerals will be used to designate the same or similar components or steps as those in each constitution and each invention-specifying matter described above in the autoserum-containing bone marrow cell culture system 1, the autoserum-containing bone marrow cell culture method, and the method for producing a medicinal composition comprising autoserum-containing cultured bone marrow cells as an active ingredient according to the present first or second embodiment, so that the description will be omitted.

The bone marrow cell culture and transport step S8 is a step that is performed in the bone marrow cell culturing device 5. In this step, the bone marrow cells contained in the prepared bone marrow cell suspension are cultured in the bone marrow cell culturing and transporting vessel 52. Also in this step, the bone marrow cell suspension prepared in a distant place is stored in the bone marrow cell culturing and transporting vessel 52 and directly transported in a cultured state. As described above, the bone marrow cell culturing and transporting vessel 52 is preferably a cell culture flask. The amount of the medium appropriate for the amount of the bone marrow fluid in the bone marrow cell suspension preparation step S1 is preferably 2 times to 4 times the amount of the bone marrow fluid. In the bone marrow cell culture and transport step S8, the bone marrow cells are preferably cultured for 4 days to 7 days in the bone marrow cell culturing and transporting vessel 52.

Figure 12:
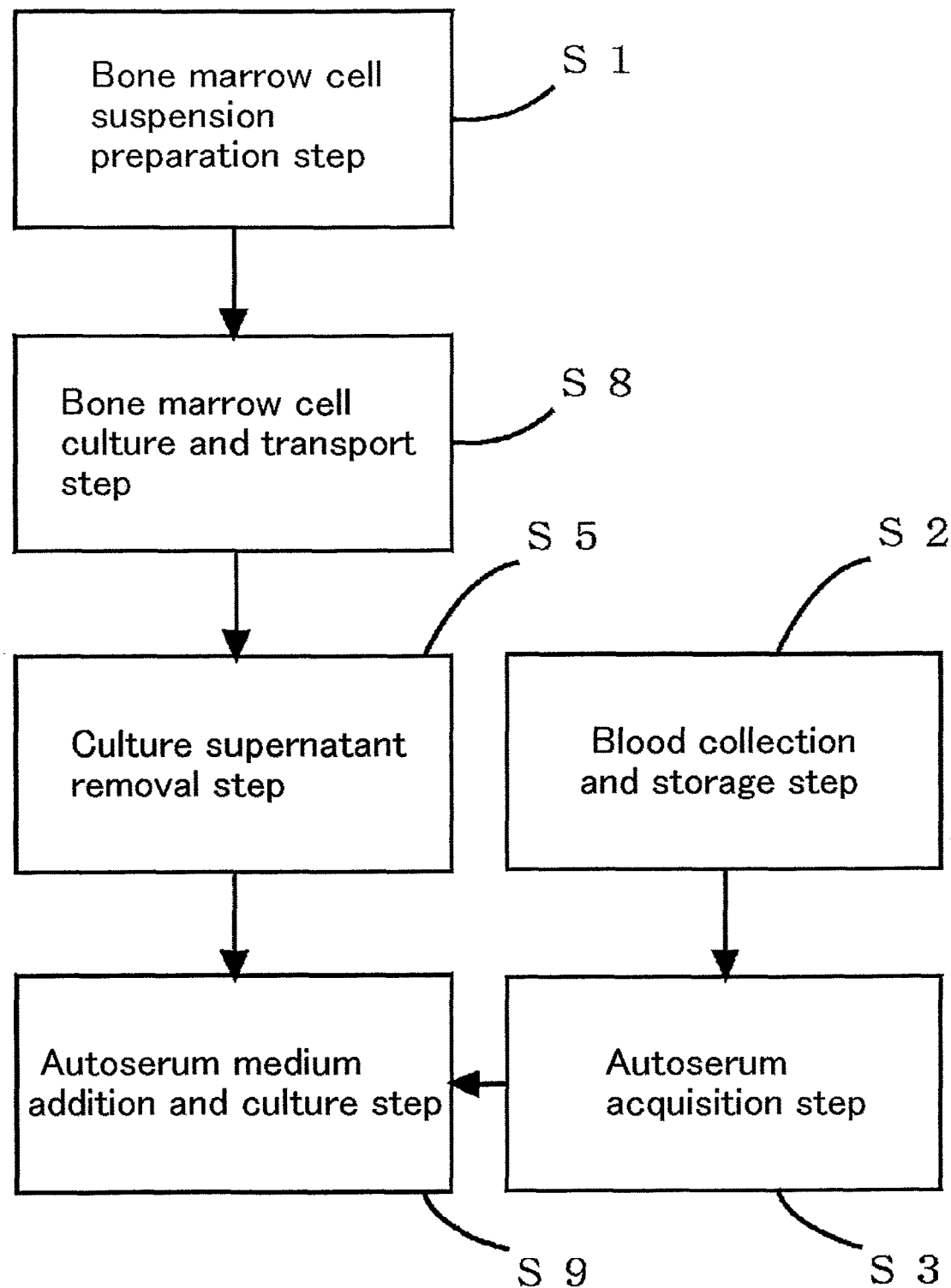
FIG. 12 is a flow chart showing the second embodiment of the method for producing a medicinal composition comprising autoserum-containing cultured bone marrow cells as an active ingredient according to the present invention.

Next, the method for producing a medicinal composition comprising autoserum-containing cultured bone marrow cells as an active ingredient according to the present second embodiment is a method for directly culturing bone marrow cells collected from a subject without use of an anticoagulant and then further culturing the resulting cells using the serum of the subject. Specifically, as shown in FIG. 12, the method comprises bone marrow cell suspension preparation step S1, bone marrow cell culture and transport step S8, blood collection and storage step S2, autoserum acquisition step S3, culture supernatant removal step S5, and autoserum medium addition and culture step S9, wherein: a bone marrow fluid is transferred at the site of collection from the bone marrow fluid storing syringe 21 to the bone marrow cell culturing and transporting vessel 52 and then mixed with a medium to perform anticoagulation while starting culture of the bone marrow cells; the resulting bone marrow cell suspension is transported in a cultured state while stored in the bone marrow cell culturing and transporting vessel 52; after a lapse of a predetermined culture period, the culture supernatant containing floating cells is removed; and at CPC, a fresh medium and the serum of the subject are added into the bone marrow cell culturing and transporting vessel 52 to perform further culture. In the invention-specifying matters of the method for producing a medicinal composition comprising autoserum-containing cultured bone marrow cells as an active ingredient according to the present second embodiment, the same reference numerals will be used to designate the same or similar components or steps as those in each constitution and each invention-specifying matter described above in the first embodiment or the autoserum-containing bone marrow cell culture system 1 and the autoserum-containing bone marrow cell culture method according to the present second embodiment, so that the description will be omitted.

The bone marrow cell culturing device 5, the blood collecting and storing device 3, autoserum acquiring device 4, and the autoserum-containing bone marrow cell culture system 1 comprising these devices according to the present second embodiment, the autoserum-containing bone marrow cell culture method, and the method for producing a medicinal composition comprising autoserum-containing cultured bone marrow cells as an active ingredient produce the following effects:

1. The bone marrow cells contained in the bone marrow fluid collected from the subject can be anticoagulated cleanly and conveniently in a liquid-tight state to efficiently obtain the bone marrow cells of interest.
2. The blood of the subject can be stored cleanly and conveniently in a liquid-tight state, and the serum thereof can be obtained efficiently.
3. The bone marrow cells of the subject can be cultured using the autoserum and thereby grown efficiently, and the resulting bone marrow cells can be used in regenerative medicine.
4. The bone marrow cells contained in the bone marrow fluid collected from the subject can be grown conveniently and reliably even when the amount of the cells is small, and the resulting bone marrow cells can be used in regenerative medicine.
5. Even the bone marrow cells contained in bone marrow fluid collected from the subject in a distant place can be cultured and grown reliably, and the resulting bone marrow cells can be used in regenerative medicine.

REFERENCE SIGNS LISTS

1: Autoserum-containing bone marrow cell culture system
2: Bone marrow cell suspension storing device
3: Blood collecting and storing device
4: Autoserum acquiring device
5: Bone marrow cell culturing device
6: Three-way stopcock for bone marrow cell suspension
7: Storing vessel lid
8: Three-way stopcock for blood collection
21: Bone marrow fluid storing syringe
22: Medium storing syringe
23: Bone marrow cell suspension transporting vessel
24: Connecting unit for bone marrow cell suspension
25: Transporting vessel lid
26: Transporting vessel tube
27: Transporting vessel vent
28: Transporting vessel vent filter
31: Vascular puncture needle
32: Blood storing vessel
33: Connecting unit for blood collection
34: Indwelling needle
35: Indwelling needle connection tube
36: Syringe for blood collection
37: Three-way connecting unit for blood collection
38: Plunger for blood collection
41: Centrifuging unit
51: Bone marrow cell culture vessel
52: Bone marrow cell culturing and transporting vessel
53: Culturing and transporting vessel lid
61: First port for suspension
62: Second port for suspension
63: Third port for suspension
64: Cock for suspension
71: Storing vessel tube
72: Storing vessel vent
73: Storing vessel vent filter
81: First port for blood collection
82: Second port for blood collection
83: Third port for blood collection
84: Cock for blood collection
S1: Bone marrow cell suspension preparation step
S2: Blood collection and storage step
S3: Autoserum acquisition step
S4: Bone marrow cell culture step
S5: Culture supernatant removal step
S6: Autoserum medium addition step
S7: Bone marrow cell suspension mixture preparation step
S8: Bone marrow cell culture and transport step
S9: Autoserum medium addition and culture step

What is claimed is:

1. A method for preparing cultured bone marrow cells from a subject without use of an anticoagulant, comprising:
   (a) collecting at a site of the subject a bone marrow fluid in a liquid-tight state without use of an anticoagulant, wherein the collected bone marrow fluid comprises bone marrow cells;
   (b) mixing the collected bone marrow fluid with a batch of a first culture medium in a liquid-tight state at the site of collection without use of an anticoagulant immediately after step (a), wherein the batch of the first culture medium is in an amount 1.5 times to 6 times the amount of the collected bone marrow fluid, whereby an anticoagulated bone marrow cell suspension comprising the bone marrow cells in the presence of the batch of the first culture medium is prepared;
   (c) transporting the anticoagulated bone marrow cell suspension in a suspended state to a location of cell culture; and
   (d) culturing the bone marrow cells in the presence, of the batch of the first culture medium used in step (b) in a bone marrow cell culture vessel at the location of cell culture, whereby the cultured bone marrow cells are prepared.

2. The method of claim 1, wherein the culturing step is performed in the presence of a serum of the subject.

3. The method of claim 1, wherein the culturing step is performed in the presence of a serum of the subject and a second culture medium.

4. The method of claim 1, further comprising:
   (e) preparing a culture supernatant comprising floating cells from the culture of step (d);
   (f) removing the culture supernatant from the bone marrow cell culture vessel to produce bone marrow cells attached to the bone marrow cell culture vessel; and
   (g) adding a medium to the attached bone marrow cells, wherein the medium comprises a serum of the subject.

5. A method for producing a medicinal composition comprising, mixing the cultured bone marrow cells from a subject prepared according to the method of claim 1 with a medium, wherein the medium comprises a serum of the subject.

6. A method for preparing cultured bone marrow cells from a subject without use of an anticoagulant, comprising:
   (a) collecting at a site of the subject a bone marrow fluid containing bone marrow cells in a liquid-tight state, wherein the collected bone marrow fluid comprises bone marrow cells;
   (b) mixing the collected bone marrow fluid with a batch of a first culture medium in a liquid-tight state at the site of collection, wherein the batch of the first culture medium is in an amount 1.5 times to 6 times the amount of the collected bone marrow fluid, whereby an anticoagulated bone marrow cell suspension comprising the bone marrow cells in the presence of the batch of the first culture medium is prepared;
   (c) directly culturing and transporting the bone marrow cells in the anticoagulated bone marrow cell suspension in a suspended state to a location of cell culture, wherein the bone marrow cells are directly cultured in the presence of the batch of the first culture medium used in step (b); and
   (d) culturing the bone marrow cells from the anticoagulated bone marrow cell suspension from step (c) in a bone marrow cell culture vessel at the location of cell culture, wherein the bone marrow cells are cultured in the presence of the batch of the first culture medium used in steps (b) and (c), whereby the cultured bone marrow cells are prepared.

7. The method of claim 6, wherein the culturing step (d) is performed in the presence of a serum of the subject.

8. The method of claim 6, wherein the culturing step (d) is performed in the presence of a serum of the subject and a second culture medium.

9. The method of claim 6, further comprising:
   (e) preparing a culture supernatant comprising floating cells from the culture of step (d);
   (f) removing the culture supernatant from the bone marrow cell culture vessel to produce bone marrow cells attached to the bone marrow cell culture vessel; and (g) adding a medium to the attached bone marrow cells, wherein the medium comprises a serum of the subject.

10. A method for producing a medicinal composition comprising, mixing the cultured bone marrow cells from a subject prepared according to the method of claim 6 with a medium, wherein the medium comprises a serum of the subject.

* * * * *